United States Patent
Chang et al.

(10) Patent No.: US 11,406,095 B2
(45) Date of Patent: Aug. 9, 2022

(54) ADHESIVE-TYPE INSECT TRAP HAVING A LIGHT SOURCE SEAT AND A LIGHT SOURCE MOUNT

(71) Applicant: SEOUL VIOSYS CO., LTD., Gyeonggi-do (KR)

(72) Inventors: Sang Hyun Chang, Gyeonggi-do (KR); Hoon Sik Eom, Gyeonggi-do (KR); Si Ho Yu, Gyeonggi-do (KR); Gwang Ryong Lee, Gyeonggi-do (KR); Sung Il Park, Gyeonggi-do (KR)

(73) Assignee: SEOUL VIOSYS CO., LTD., Gyeonggi-do (KR)

( * ) Notice: Subject to any disclaimer, the term of this patent is extended or adjusted under 35 U.S.C. 154(b) by 310 days.

(21) Appl. No.: 16/477,153

(22) PCT Filed: Jan. 8, 2018

(86) PCT No.: PCT/KR2018/000350
§ 371 (c)(1),
(2) Date: Jul. 10, 2019

(87) PCT Pub. No.: WO2018/131853
PCT Pub. Date: Jul. 19, 2018

(65) Prior Publication Data
US 2019/0350184 A1    Nov. 21, 2019

(30) Foreign Application Priority Data

Jan. 10, 2017 (KR) .................. 10-2017-0003381
May 25, 2017 (KR) .................. 10-2017-0064772
Jun. 22, 2017 (KR) .................. 10-2017-0079263

(51) Int. Cl.
*A01M 1/14* (2006.01)
*A01M 1/02* (2006.01)
(Continued)

(52) U.S. Cl.
CPC ................ *A01M 1/14* (2013.01); *A01M 1/02* (2013.01); *A01M 1/106* (2013.01); *A01M 1/145* (2013.01);
(Continued)

(58) Field of Classification Search
CPC ........... A01M 1/14; A01M 1/04; A01M 1/145
See application file for complete search history.

(56) References Cited

U.S. PATENT DOCUMENTS 4,876,822 A * 10/1989 White ................... A01M 1/145
                                                        43/113
5,651,211 A *  7/1997 Regan ................... A01M 1/145
                                                        43/113
(Continued)

FOREIGN PATENT DOCUMENTS

CN        203087336        7/2013
CN        203897100       10/2014
(Continued)

OTHER PUBLICATIONS

Supplementary European Search Report issued in European Application No. 18738568.7, dated Sep. 11, 2020.
(Continued)

*Primary Examiner* — Peter M Poon
*Assistant Examiner* — Shada Mohamed Alghailani
(74) *Attorney, Agent, or Firm* — Burris Law, LLC

(57) ABSTRACT

An adhesive-type insect trap includes a body having a hole for insertion of an adhesive sheet; a light source mounting unit disposed on the body; and a cover which is detachably mounted on the body and has a through-hole in at least a part thereof. The body further includes a light source seating unit provided so as to correspond to the light source mounting unit, and a light source may have one side thereof mounted
(Continued)

on the light source mounting unit and the other side thereof seated on the light source seating unit.

7 Claims, 33 Drawing Sheets

(51) Int. Cl.
    *A01M 1/16*     (2006.01)
    *A01M 1/10*     (2006.01)
    *G01J 1/44*     (2006.01)
    *G01V 8/12*     (2006.01)

(52) U.S. Cl.
    CPC ............... *A01M 1/165* (2013.01); *G01J 1/44* (2013.01); *G01V 8/12* (2013.01)

(56) References Cited

U.S. PATENT DOCUMENTS

| | | | | |
|---|---|---|---|---|
| 5,950,355 | A * | 9/1999 | Gilbert | A01M 1/145 43/113 |
| 8,739,461 | B2 * | 6/2014 | Studer | A01M 1/145 43/114 |
| 10,104,879 | B2 * | 10/2018 | McGowan | A01M 1/223 |
| 2002/0032980 | A1 | 3/2002 | Nelson | |
| 2002/0083639 | A1 * | 7/2002 | Perry | A01M 1/026 43/114 |
| 2003/0089024 | A1 | 5/2003 | Nelson et al. | |
| 2007/0124987 | A1 * | 6/2007 | Brown | A01M 1/023 43/113 |
| 2017/0006848 | A1 * | 1/2017 | Barroso | A01M 29/10 |
| 2018/0199565 | A1 * | 7/2018 | Zosimadis | A01M 23/00 |
| 2018/0317473 | A1 * | 11/2018 | Gries | A01M 1/04 |
| 2019/0000059 | A1 * | 1/2019 | Marka | A01M 31/002 |

FOREIGN PATENT DOCUMENTS

| | | |
|---|---|---|
| GB | 2459717 | 11/2009 |
| JP | 2009-043635 | 2/2009 |
| JP | 4256441 | 4/2009 |
| JP | 2009183164 | 8/2009 |
| JP | 5216054 | 6/2013 |
| JP | 2016509843 | 4/2016 |
| KR | 1020080107918 | 12/2008 |
| KR | 2020080006034 | 12/2008 |
| KR | 100895486 | 5/2009 |
| KR | 100895489 | 5/2009 |
| KR | 10-2009-0064070 | 6/2009 |
| KR | 100968199 | 7/2010 |
| KR | 1020100078422 | 7/2010 |
| KR | 1020120073476 | 7/2012 |
| KR | 1020120139354 | 12/2012 |
| KR | 101266861 | 5/2013 |
| KR | 101573714 | 12/2015 |
| KR | 2020160001863 | 6/2016 |
| KR | 10-2016-0098791 | 8/2016 |
| KR | 101681743 | 12/2016 |
| WO | 2016207430 | 12/2016 |

OTHER PUBLICATIONS

Supplementary European Search Report issued in European Application No. 18738947.3, dated Sep. 11, 2020.
International Search Report for International Application No. PCT/KR2018/000350, dated Apr. 26, 2018.
International Search Report for International Application No. PCT/KR2018/000268 dated Apr. 24, 2018.
International Search Report for International Application No. PCT/KR2018/000344, dated Apr. 25, 2018.
Office Action issued in Chinese Application No. 2018800172042, dated Mar. 3, 2021.
Office Action issued in Indian Application No. 201937032046; dated Jan. 18, 2021.
Office Action issued in corresponding Indonesian Application No. P00201906980, dated Apr. 1, 2021.

* cited by examiner

4000

6000

7000

9000

270

370

470

Adhesive-type insect trap

ADHESIVE-TYPE INSECT TRAP HAVING A LIGHT SOURCE SEAT AND A LIGHT SOURCE MOUNT

RELATED APPLICATIONS

The present application is a U.S. national stage application under 35 U.S.C. § 371 of PCT Application No. PCT/KR2018/000350 filed Jan. 8, 2018, which claims priority to Korean Application Nos. 10-2017-0003381 filed Jan. 10, 2017, 10-2017-0064772 filed May 25, 2017, and 10-2017-0079263 filed Jun. 22, 2017, all of which are hereby incorporated in their entirety by reference as set forth herein.

TECHNICAL FIELD

The present disclosure relates to an adhesive-type insect trap and, more particularly, to an adhesive-type insect trap adapted to collect insects by attracting the insects using a light source and attaching the enticed insects thereto. The present disclosure further relates to an adhesive-type insect trap having a light source seat and a light source mount for accommodating a light source.

RELATED ART

Generally, flying insects such as flies, mosquitoes, and moths are infectious vectors that carry various kinds of germs, and cause direct or indirect damage to humans or crops.

Although various pesticides and insecticides have been used to eliminate such harmful insects, such pesticides and insecticides are harmful to a human body and cause ecological imbalance. As an alternative, various methods, such as development of biodegradable insecticides, use of natural enemies or pheromones, and application of insecticide after attraction of insects, have been studied.

As an example of application of insecticide after attraction of insects, there is a so-called electric insecticidal apparatus in which an infrared (IR) heater lamp is mounted inside a main body of the apparatus in order to attract insects exhibiting positive phototaxis to move from the periphery to bright light such that insects attracted to the heater lamp side are electrically charged by heat from the heater lamp. However, due to use of high voltage, the apparatus has problems of high power consumption and risk of electric shock, generating noise and an odor upon electric shock of an insect, and scattering an insect pollutant or a fragment thereof.

In order to solve such problems of the electric insecticidal apparatus, an insect trap using a flypaper-type adhesive sheet has been developed. However, this insect trap has problems in that an insect trapped in the insect trap is seen from the outside, providing an unpleasant feeling to a user, in that a light source mounted on the insect trap has significantly low attraction efficiency, in that the adhesive sheet is likely to adhere to the insect trap upon insertion into the insect trap, or in that the adhesive sheet is easily released after insertion into the insect trap.

SUMMARY

Embodiments of the present disclosure provide an adhesive-type insect trap that collects insects by attracting the insects to move towards the insect trap using a light source and has high trapping efficiency while preventing the insects from being directly visibly observed from the outside.

Embodiments of the present disclosure provide an adhesive-type insect trap that prevents an adhesive sheet from being attached to the insect trap upon insertion into the insect trap and that allows the adhesive sheet to be secured to a main body of the insect trap after insertion into the insect trap.

Embodiments of the present disclosure provide an adhesive-type insect trap that includes a photocatalyst generating a deodorization effect.

Embodiments of the present disclosure provide an adhesive-type insect trap that can generate not only light but also a gas such as carbon dioxide, as an element for attraction of mosquitoes.

Embodiments of the present disclosure provide an adhesive-type insect trap that is provided with a light source for sterilization to sterilize the interior of the insect trap or to kill insects trapped by an adhesive sheet.

Embodiments of the present disclosure provide an adhesive-type insect trap that is provided with a camera capable of observing or photographing insects collected therein.

Embodiments of the present disclosure provide an adhesive-type insect trap that is provided with a sensor for detecting the kind of insect trapped therein, an area of an adhesive sheet trapping insects, brightness of the adhesive sheet, an ambient temperature or illuminance of a light source, the intensity of light emitted from the light source, presence of the adhesive sheet in the insect trap, attachment of a cover to the insect trap, and the like, for adjusting the intensity of light emitted from the light source, or for supplying electric power to the light source depending upon the presence of the adhesive sheet in the insect trap or the attachment of the cover to the insect trap.

Embodiments of the present disclosure provide an adhesive-type insect trap that further includes an insect attractant spray or includes an insect attractant contained in an adhesive sheet to improve insect attraction efficiency.

DETAILED DESCRIPTION OF EMBODIMENTS

Figure 1:
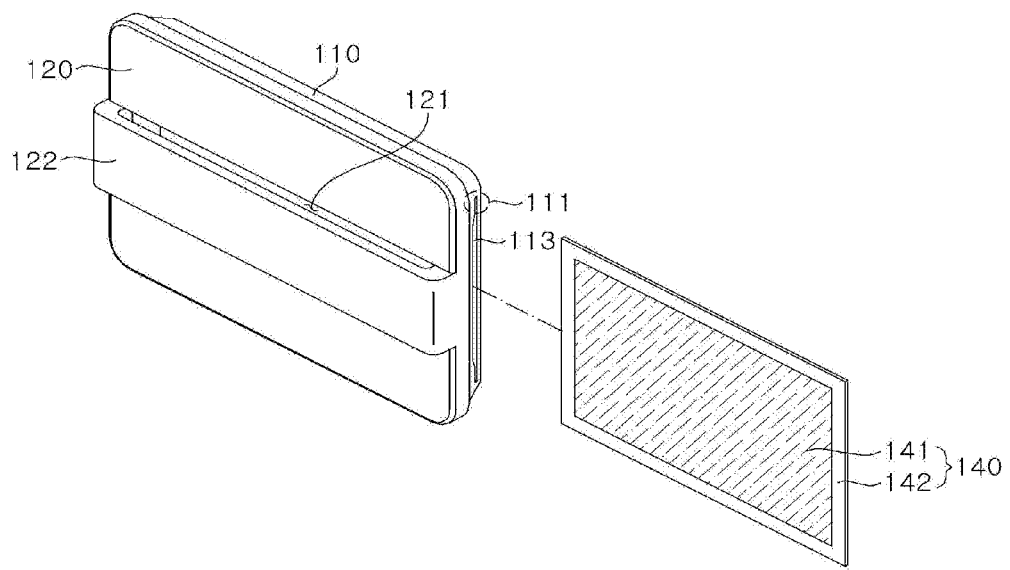
FIG. 1 and FIG. 2 show an adhesive-type insect trap according to one embodiment of the present disclosure.

It should be understood that the present disclosure may be embodied in different ways and is not limited to the following embodiments, which are provided for complete disclosure and thorough understanding of the present disclosure by those skilled in the art.

Herein, when an element such as a layer or a film is referred to as being placed "on" or "under" another element, it can be directly placed "on" or "under" the other element, or intervening element(s) may be present therebetween. Herein, spatially relative terms such as "upper" and "lower" are defined with reference to the accompanying drawings. Thus, it will be understood that the term "upper surface" can be used interchangeably with the term "bottom surface".

Like components will be denoted by like reference numerals throughout the accompanying drawings. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

As used herein, the term "insect" may refer to various kinds of flying insects, particularly flies, without being limited thereto, and a light source may be selected from various kinds of light sources, for example, a UV LED, without being limited thereto.

One aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the main body further includes a light source seat disposed to face the light source mount such that one side of a light source is mounted on the light source mount and the other side of the light source is mounted on the light source seat.

In one embodiment, the light source seat may include: a pressing member pressing the light source in a thickness direction of the light source; a securing member pressing the light source in a height direction of the light source; and a support plate supporting the pressing member and the securing member.

In one embodiment, the light source may include an end cap adjoining the light source seat and the end cap may include at least one planar surface and at least one curved surface. In one embodiment, the securing member may include a tongue portion adjoining the light source and a flat portion extending from the tongue portion and adjoining the support plate.

In one embodiment, the securing member may adjoin the planar surface of the end cap and the pressing member may adjoin the curved surface of the end cap. In one embodiment, the pressing member may include a pressing member flat portion extending from the support plate in the height direction of the light source and a pressing member bent portion bent from the pressing member flat portion toward the light source. In one embodiment, the pressing member bent portion may press the curved surface of the end cap in the thickness direction of the light source and the tongue portion may press the planar surface of the end cap in the height direction of the light source. In one embodiment, the pressing member bent portion may adjoin the curved surface of the end cap at a location higher than half a height of the end cap. In one embodiment, an angle α formed between a point at which the pressing member bent portion contacts the end cap and the planar surface of the end cap may be greater than 0° and less than 50°.

In one embodiment, when the light source is seated on the light source seat, restoration force of the pressing member flat portion acting on the light source may be different from restoration force of the pressing member bent portion acting on the light source. In one embodiment, the insect trap may further include at least one light source support member supporting the light source mounted on the light source mount. In one embodiment, the light source support member may include a flat plate separated a predetermined distance from a main body bottom such that the light source is seated on the flat plate. In one embodiment, the light source support member includes at least one light source-pressing member pressing the light source in a thickness direction of the light source. In one embodiment, the light source may include a case and an end cap disposed at a distal end of the case, and the light source-pressing member may adjoin the case at a location higher than half (½) a height of the case. In one embodiment, a portion of the light source support member adjoining the light source includes at least one metal selected from among Ag, Cu, Au, Al, and Mo.

Another aspect of the present disclosure provides an adhesive-type insect trap including: a main body having an adhesive sheet insertion hole; a light source mount disposed on the main body; and a cover detachably attached to the main body and having a through-hole formed in at least a portion thereof, and the adhesive-type insect trap further includes a sensor. In one embodiment, the main body may further include a side portion connected to at least a portion of the light source mount, and the side portion may be provided with a sensor installation unit on which the sensor is disposed. In one embodiment, the sensor installation unit may include a sensor seat and a sensor guide guiding light emitted from an outside of the insect trap to reach the sensor seat. In one embodiment, the sensor installation unit may further include a sensor installation unit protrusion protruding from the side portion. In one embodiment, the sensor installation unit may be provided with an illuminance sensor.

In one embodiment, the side portion may be further provided with a display unit. In one embodiment, the display unit may include an indication light source seat and an indication light source guide guiding light emitted from the indication light source seat to reach an outside of the side portion. In one embodiment, the sensor may detect at least one of the kind of insect trapped on the adhesive sheet, an area of the adhesive sheet trapping insects, brightness of the adhesive sheet, an ambient temperature of the light source, the intensity of light emitted from the light source, ambient illuminance of the insect trap, a time for replacement of the adhesive sheet, insertion of the adhesive sheet into the insect trap, and attachment of the cover to the insect trap. In one embodiment, the sensor may include a UV sensor measuring the intensity of light emitted from the light source. In one embodiment, the light source mounted on the light source mount may include a light emitting diode and the UV sensor may measure the intensity of light emitted from the light emitting diode.

In one embodiment, when the intensity of light emitted from the light emitting diode and measured by the UV sensor is less than a preset value, the insect trap may generate a light source replacement signal. In one embodiment, the light source may include a plurality of light emitting diodes and the plurality of light emitting diodes may be controlled to be sequentially turned on/off. In one embodiment, the sensor may include an illuminance sensor detecting illuminance of ambient light around the adhesive-type insect trap. In one embodiment, drive voltage applied to the light source mounted on the light source mount may be controlled through PWM (Pulse width Modulation) depending upon variation in illuminance of ambient light detected by the illuminance sensor. In one embodiment, the drive voltage applied to the light source may have at least two duty ratios.

In one embodiment, assuming a duty ratio of the drive voltage applied to the light source is s % when the illuminance of ambient light detected by the illuminance sensor is less than a preset illuminance range and is b % when the illuminance of ambient light detected by the illuminance sensor exceeds the preset illuminance range, the duty ratios of the drive voltage may satisfy a relationship: b>s. In one embodiment, the illuminance sensor may include at least three preset illuminance ranges and the drive voltage applied to the light source may be controlled to have a duty ratio changed depending upon variation in illuminance range. In one embodiment, the sensor includes a photosensor emitting and detecting IR light to measure an amount of trapped insects. In one embodiment, the photosensor is disposed at least one side of the through-hole. In one embodiment, the photosensor is disposed at least one side of the adhesive sheet.

In one embodiment, the adhesive type insect trap may further include a camera capable of detecting information on insects trapped therein. In one embodiment, the information on insects may include the information on insects may include at least one of the kind of insect and an area of the adhesive sheet trapping the insects. In one embodiment, the camera may be attached to a rear side of the cover. In one embodiment, the light source mounted on the light source mount may include a support member and a light emitting diode disposed on the support member, and the sensor may include a UV sensor provided to the support member to measure the intensity of light emitted from the light source.

Hereinafter, embodiments of the present disclosure will be described in more detail with reference to the accompanying drawings. FIG. 1 shows an adhesive-type insect trap according to one embodiment of the present disclosure. Referring to FIG. 1, an adhesive-type insect trap 1000 includes a main body 110 and a cover 120, and may receive an adhesive sheet 140 inserted therein.

The main body 110 may have a shape corresponding to a shape of the adhesive sheet 140 guided into the main body 110 instead of having a particular shape. For example, the main body 110 may include a casing having a hexahedral shape in which an adhesive sheet 140 having a plate shape is guided, and may be formed of a plastic material generally used in the art in order to allow the insect trap to be used indoors or outdoors for a long period of time while preventing excessive increase in manufacturing costs, without being limited thereto.

In addition, the main body 110 includes an adhesive sheet insertion hole 113 formed on a front surface of the main body 110 such that the adhesive sheet 140 can be inserted in an upright posture into the main body 110 in a vertically sliding manner or in a horizontally sliding manner, and a guide groove 111 formed on at least one side of the adhesive sheet insertion hole 113 to guide the adhesive sheet 140. The guide groove 111 may be configured to receive an edge of the adhesive sheet 140 inserted into the main body 110, may have a thickness corresponding to a thickness of the adhesive sheet 140 to allow easy insertion and separation of the adhesive sheet 140 and a depth corresponding to a length preventing a flypaper piece 141 of the adhesive sheet 140 from contacting the main body 110. By way of example, the adhesive sheet insertion hole 113 may have an open shape or a closed shape opened or closed by a door (not shown), which may have any shape and may be configured to block or open at least a portion of the adhesive sheet insertion hole 113.

The cover 120 may have any shape without being limited to a particular shape and may be detachably attached to a front side of the main body 110. The cover 120 may have a through-hole 121 formed in at least a portion thereof to allow insects to pass therethrough, may be formed of a material allowing light emitted from a light source 170 mounted on a light source mount 130 to pass therethrough, and may have a roughened surface or may be provided with a separate cover sheet attached to or spaced apart from a front side or a rear side of the cover 120 to allow refraction or diffusion of the light. The cover 120 may be rotatably disposed on the main body 110 such that a user can change the location of the cover 120 depending upon user environment. Further, the cover 120 may be detachably attached to the main body 110 through sliding movement or by a magnet in order to prevent damage to components of the adhesive-type insect trap 1000 such as the adhesive sheet 140 and the like due to application of excessive force to the cover 120 to separate the cover 120 from the main body 110 by a user. Further, the cover 120 may be connected to the main body 110 through a ring, a chain or a string formed of a stretchable material. Alternatively, the cover 120 may be secured at one side thereof to the main body 110 and detachably coupled at the other side thereof to the main body 110 to prevent the cover 120 from being completely separated from the main body 110.

By way of example, at least a portion or the entirety of the cover 120 may be formed of a light transmissive material. For example, a portion of the cover 120 through which light emitted from the light source 170 passes may comprise polycarbonate (PC), polyethylene terephthalate (PET), methacrylate-styrene (MS), poly(methyl methacrylate) (PMMA), or the like, and may have at least one of transparent, translucent and opaque colors.

The cover 120 may have a through-hole blocking structure 122 adapted to block at least a portion of the through-hole 121. The through-hole blocking structure 122 may have any shape capable of blocking at least a portion of the through-hole 121 and may be integrally formed with the cover 120 or may be detachable from the cover 120. In addition, the through-hole blocking structure 122 may extend from the cover 120 to protrude outward from the cover 120 or may be formed by a convex or concave portion of the cover 120. By way of example, referring to FIG. 1, the through-hole blocking structure 122 may be realized by a protruded portion relative to the cover 120.

That is, the adhesive-type insect trap 1000 has the through-hole blocking structure 122 adapted to block the adhesive sheet 140 from being visible from the outside, thereby preventing insects attached to the adhesive sheet 140 from being observed from the outside.

The adhesive sheet 140 may include a flypaper piece 141 applied to or coated onto a sheet 142. For example, the flypaper piece 141, which is a pressure sensitive adhesive material, is deposited or coated on one surface of a paper sheet to trap insects attached to the adhesive material. Here, instead of being applied to or coated onto the entire surface of the sheet 142, the flypaper piece 141 may be partially applied to or coated onto the sheet 142 to expose at least a portion of the sheet 142 such that a user can easily replace the adhesive sheet without a separate gripper formed on the sheet 142 while preventing the flypaper piece 141 from being adhered to the adhesive sheet insertion hole 113 or the guide groove 111.

Figure 2:
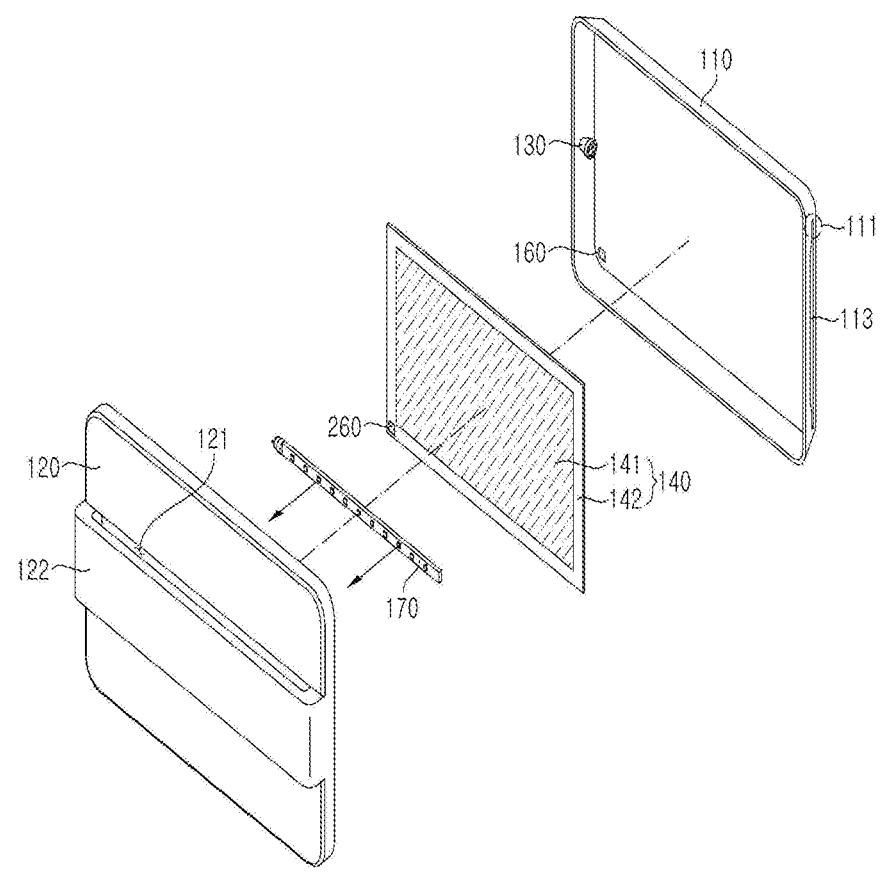

Referring to FIG. 2, the main body 110 and the adhesive sheet 140 may include magnet members 160, 260 disposed to face each other and having opposite polarities, respectively. That is, the adhesive sheet 140 may be prevented from being separated from the main body even upon rotation of an adhesive-type insect trap 2000 after installation of the adhesive sheet 140 to the main body 110 by a user.

Referring again to FIG. 2, the adhesive-type insect trap 2000 may further include the light source mount 130 received in the main body 110. The light source mount 130 is provided with the light source 170, which not only acts as a lighting fixture but also emits light for attraction of insects or light, for example, UVC light, for sterilization of insects or bacteria in the insects collected in the insect trap. The light source mount 130 may include a socket and may be disposed in any direction including a longitudinal direction and a transverse direction.

The light source 170 emits light having a wavelength capable of attracting insects and the main body 110 may be provided with at least one light source therein. For example, the light source 170 may emit UV light having a wavelength of 350 nm to 400 nm, at which the light source 170 can efficiently attract insects exhibiting positive phototaxis to move from the periphery to bright light, thereby improving insect attraction efficiency without providing harmful influence to a user body.

The adhesive sheet 140 may be provided to at least one of a front side, a rear side and lateral sides of the light source mount 130 and may be formed of a transparent material or an opaque material depending upon installation locations of the adhesive sheet 140 and the light source mount 130. For example, when light emitted from the light source 170 is emitted outside the cover 120 after passing through the adhesive sheet 140, both the flypaper piece 141 and the sheet 142 of the adhesive sheet 140 may be formed of a light transmissive material or at least one of the flypaper piece 141 and the sheet 142 may be formed of a light transmissive material, for example, a material having high UV light transmittance, to allow light emitted from the light source 170 to pass therethrough.

Figure 3:
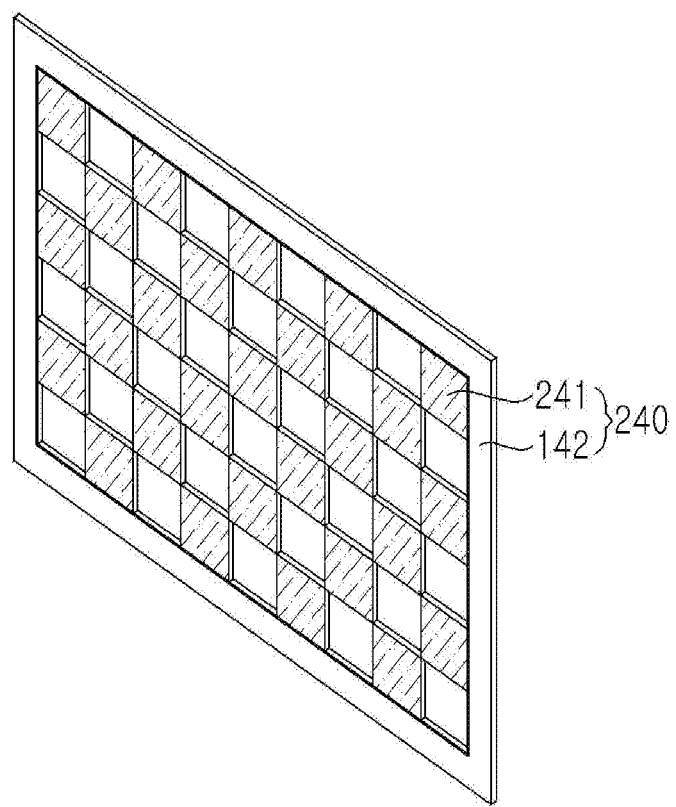
FIG. 3 and FIG. 4 show an adhesive sheet according to embodiments of the present disclosure.
Figure 4:
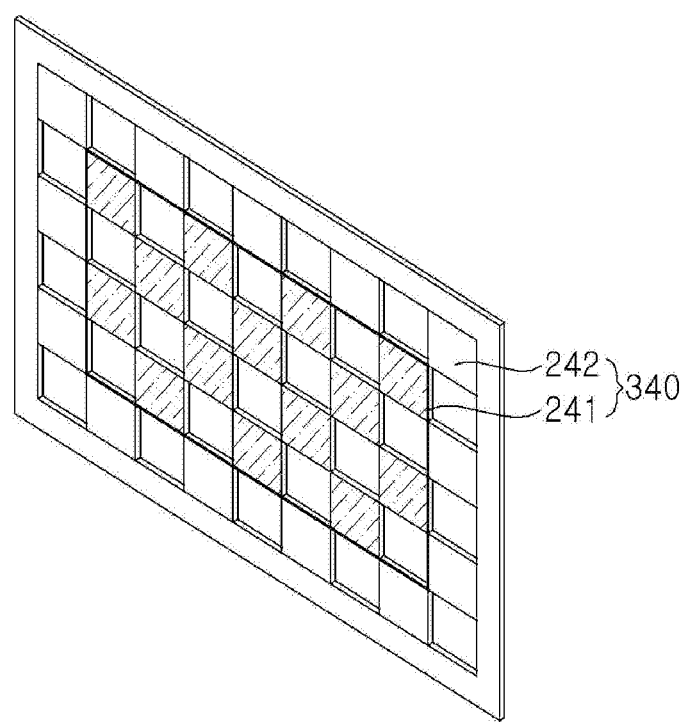

For example, referring to FIG. 3, an adhesive sheet 240 includes a sheet 142 formed of a transparent material and a flypaper piece 241 formed of an opaque material. In this example, the flypaper piece 241 may be disposed in a lattice shape or may be disposed to form punching holes. Alternatively, referring to FIG. 4, in an adhesive sheet 340, both a sheet 242 and the flypaper piece 241 may be disposed in a lattice shape or may be disposed to form punching holes, and the punching holes formed through the sheet 242 and the flypaper piece 241 at least partially overlap each other to allow light emitted from the light source 170 to pass therethrough. Here, each frame of the lattice shape may have a smaller size than insects, for example, flies, and may have a length of 2 mm to 8 mm.

FIG. 5 to FIG. 10 show various embodiments of the light source 170 and the adhesive sheet 140 disposed on an adhesive-type insect trap 3000, 4000, 5000, 6000, 7000 or 8000. In this drawings, the light source 170 is shown instead of the light source mount 130, in order to allow a person having ordinary knowledge in the art to clearly understand arrangement of the light source 170 and the adhesive sheet 140 on each insect trap. The light source 170 may be a sheet light source or a spot light. In FIG. 5 through FIG. 10, a spot light source is shown by way of example.

Figure 5:
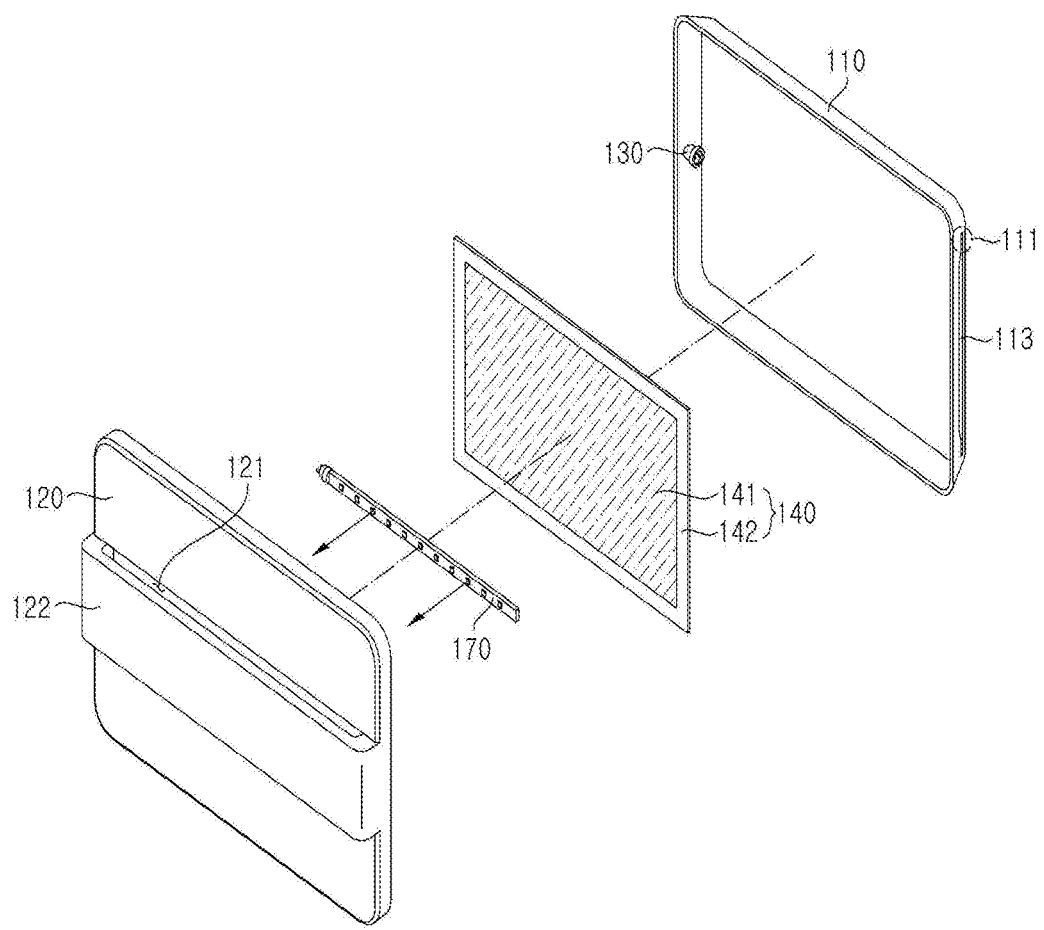
FIG. 5 shows an adhesive-type insect trap having a light source disposed in a space between an adhesive sheet and a cover according to an embodiment of the present disclosure.
Figure 6:
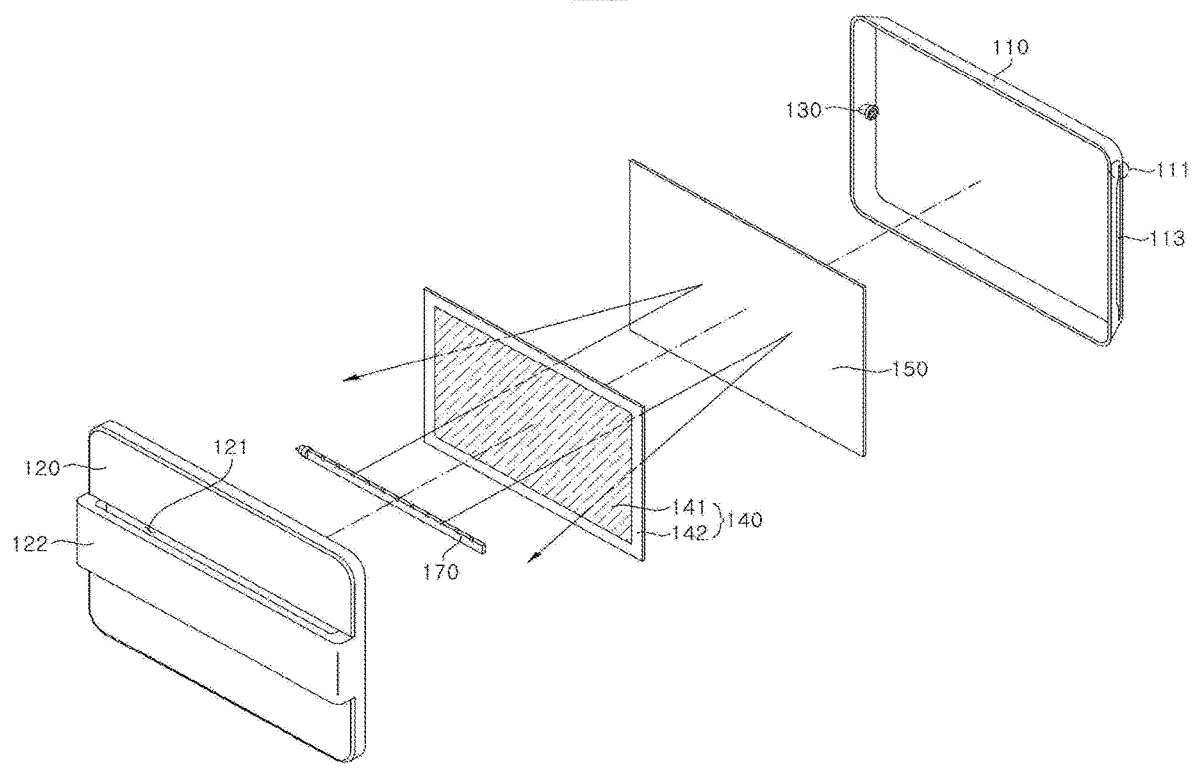
FIG. 6 shows an adhesive-type insect trap having a light source disposed in a space between an adhesive sheet and a cover and having a reflector between the adhesive sheet and a main body according to an embodiment of the present disclosure.
Figure 7:
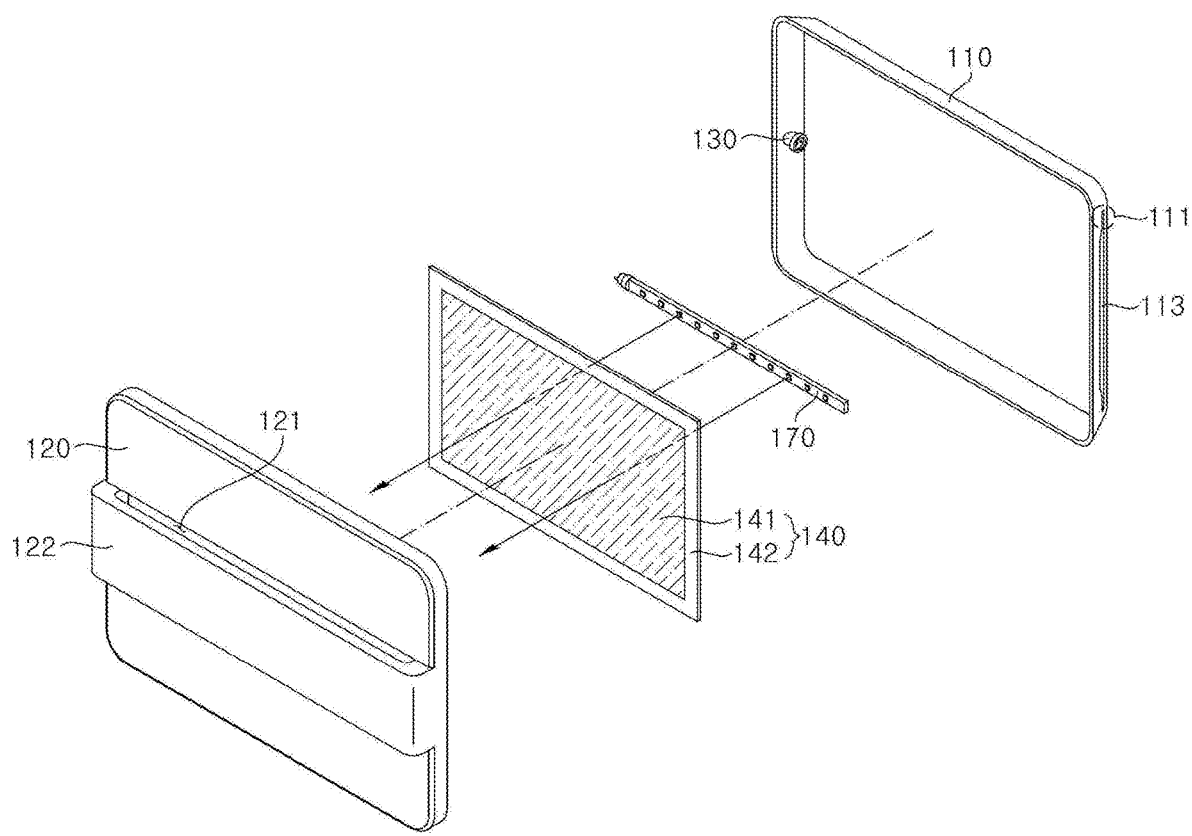
FIG. 7 shows an adhesive-type insect trap having a light source disposed in a space between an adhesive sheet and a main body according to an embodiment of the present disclosure.
Figure 8:
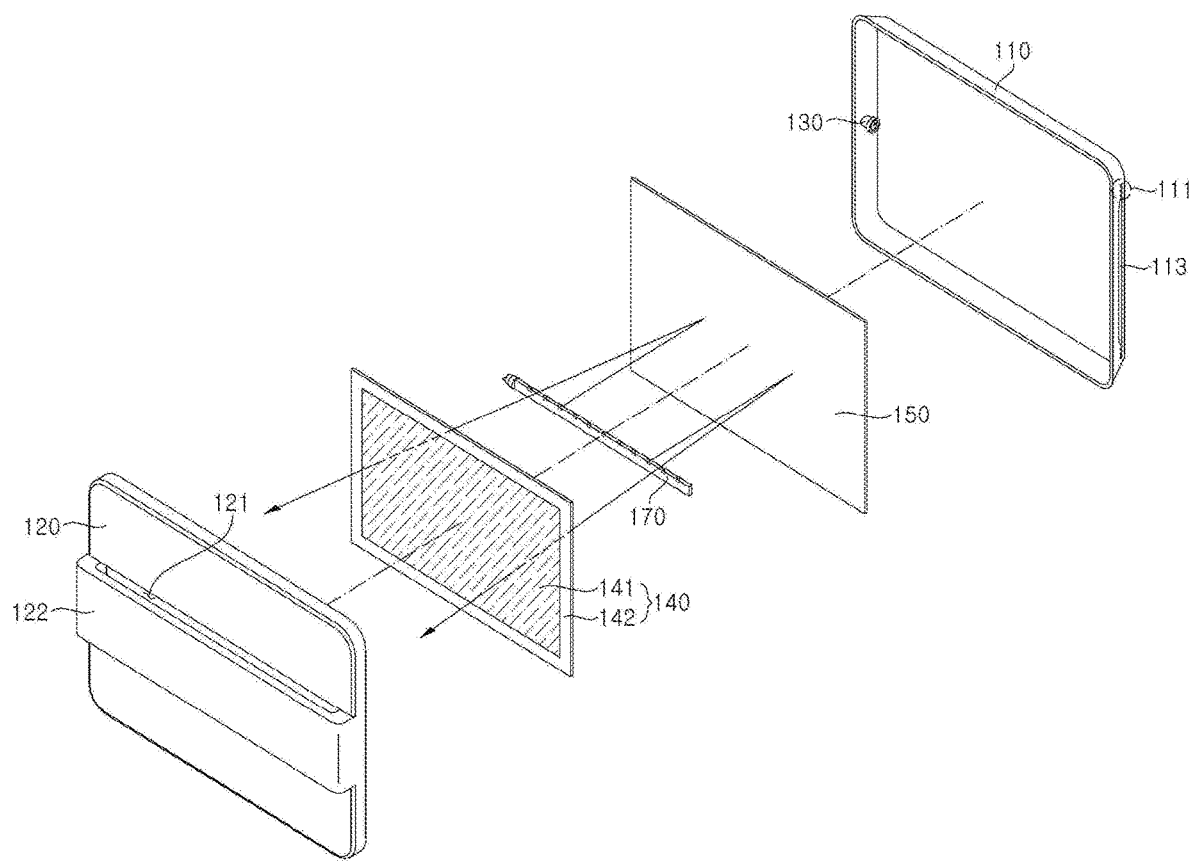
FIG. 8 shows an adhesive-type insect trap having a light source and a reflector between an adhesive sheet and a main body according to an embodiment of the present disclosure.
Figure 9:
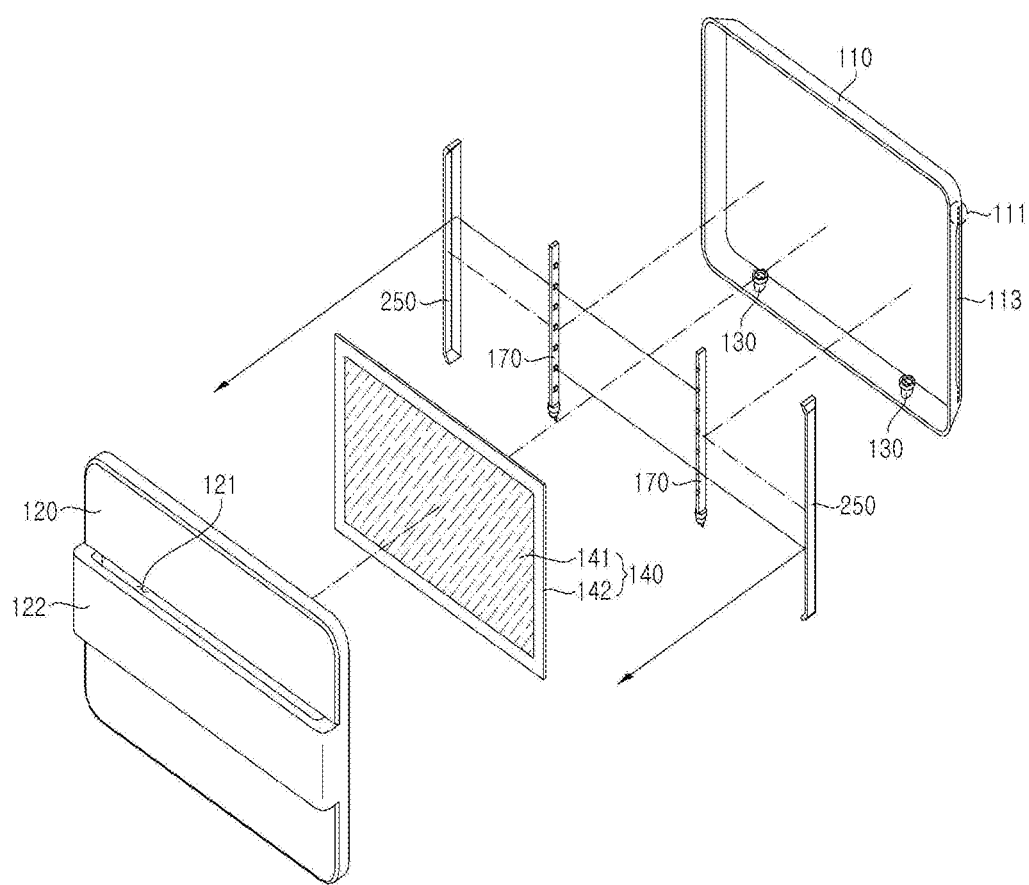
FIG. 9 shows an adhesive-type insect trap having plural light sources according to an embodiment of the present disclosure.
Figure 10:
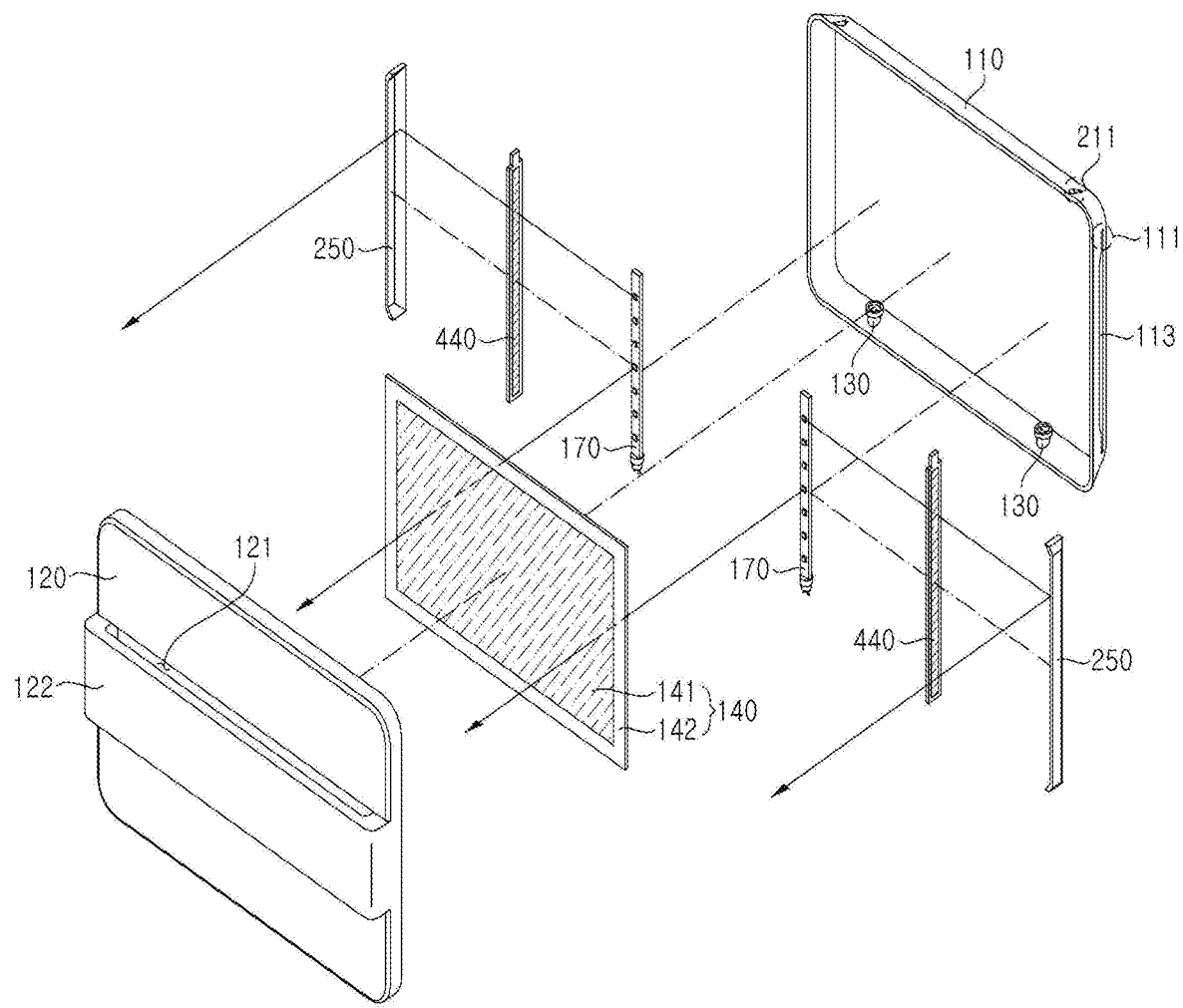
FIG. 10 shows an adhesive-type insect trap having a different light emission direction than the adhesive-type insect trap of FIG. 9 and having additional adhesive sheets according to an embodiment of the present disclosure.

FIG. 5 shows an adhesive-type insect trap having a light source disposed in a space between an adhesive sheet and a cover according to an embodiment of the present disclosure. FIG. 6 shows an adhesive-type insect trap having a light source disposed in a space between an adhesive sheet and a cover and having a reflector between the adhesive sheet and a main body according to an embodiment of the present disclosure. FIG. 7 shows an adhesive-type insect trap having a light source disposed in a space between an adhesive sheet and a main body according to an embodiment of the present disclosure. FIG. 8 shows an adhesive-type insect trap having a light source and a reflector between an adhesive sheet and a main body according to an embodiment of the present disclosure. FIG. 9 shows an adhesive-type insect trap having plural light sources according to an embodiment of the present disclosure. FIG. 10 shows an adhesive-type insect trap having a different light emission direction than the adhesive-type insect trap of FIG. 9 and having additional adhesive sheets according to an embodiment of the present disclosure.

Referring to FIG. 5, in the adhesive-type insect trap 3000, the light source 170 may be disposed in a space between the adhesive sheet 140 and the cover 120 such that light emitted from the light source 170 is directed towards the cover 120, and the adhesive sheet 140 may be formed to allow or prevent light transmission therethrough. The adhesive-type insect trap 3000 does not require additional reflectors 150, 250, a reflective sheet 143, or the flypaper pieces 141, 241, thereby enabling reduction in manufacturing costs.

Referring to FIG. 6, the adhesive-type insect trap 4000 may further include a reflector 150 disposed between the adhesive sheet 140 and the main body 110, in which the light source 170 may be disposed in a space between the adhesive sheet 140 and the cover 120 such that light emitted from the light source 170 is directed towards the main body 110. As described above, the adhesive sheet 140 may be formed of a light transmissive material or may partially have a lattice shape to allow light emitted from the light source 170 to pass therethrough. Insects, particularly flies, tend to be more strongly attracted to refracted or diffused light than to direct light. Thus, the adhesive-type insect trap 4000 is configured to allow light emitted from the light source 170 to pass through the adhesive sheet 140 at least once, instead of directly passing through the cover, thereby improving insect attraction efficiency with decoy light.

Referring to FIG. 7, the adhesive-type insect trap 5000 includes the light source 170 disposed in a space between the adhesive sheet 140 and the main body 110 such that light emitted from the light source 170 is directed towards the adhesive sheet 140 and the cover 120 to be refracted or spread instead of directly irradiating insects, thereby improving insect attraction efficiency with decoy light.

Referring to FIG. 8, the adhesive-type insect trap 6000 may further include the reflector 150 between the light source 170 and the main body 110, in which the light source 170 may be disposed in a space between the adhesive sheet 140 and the reflector 150 such that light emitted from the light source 170 is directed towards the reflector 150. With the structure that prevents light from directly reaching the adhesive sheet 140 and insects while allowing the light to be refracted or spread, the flypaper piece applied to the adhesive sheet 140 can be prevented from being deformed by light or heat while improving insect attraction efficiency with decoy light.

The adhesive-type insect trap 7000 or 8000 may include a plurality of light sources 170, which may be disposed in a direction in which the flypaper piece 141 of the adhesive sheet 140 is disposed, in an opposite direction thereto, or on a side surface. By way of example, referring to FIG. 9, in the adhesive-type insect trap 7000, the plural light sources 170 are disposed to face each other in opposite directions such that light emitted from one light source 170 is directed to another light source 170 disposed in an opposite direction to the one light source 170, and each reflector 250 may be disposed in an opposite direction to a direction in which each light source 170 emits light. By way of example, the reflector 250 includes a flat reflective surface and a bent portion formed at each side of the reflective surface except for sides of the reflective surface adjacent to the cover to allow light to be directed towards the cover. By way of example, the adhesive-type insect trap 7000 includes the plurality of light sources 170 disposed in a space between the adhesive sheet 140 and the main body 110, and allows light emitted from each of the light sources 170 to sequentially pass through the adhesive sheet 140 and the cover 120 after being reflected by the reflector 250 disposed at a rear side of the light source 170 disposed in an opposite direction thereto, thereby improving insect attraction efficiency through refraction and diffusion of light.

Referring to FIG. 10, the adhesive-type insect trap 8000 has a different light emission direction than the adhesive-type insect trap 7000 shown in FIG. 9 and may further include additional adhesive sheets 440. For example, the adhesive-type insect trap 8000 may further include the adhesive sheets 440, each of which is disposed between the light source 170 and the reflector 250 along a guide groove 211 formed on the main body 110, such that each of the light sources 170 emits light towards the reflector 250 adjacent thereto and the adhesive sheet 140 disposed corresponding to the front side of the main body 110. That is, the adhesive-type insect trap 8000 allows light emitted from the light sources 170 to be refracted and spread, thereby improving insect attraction efficiency with decoy light, and is provided with the adhesive sheets 440 not only at the front side of the main body 110 but also at lateral sides thereof, thereby improving insect trapping efficiency and capacity.

On the other hand, the adhesive-type insect trap 3000, 4000, 5000, 6000, 7000 or 8000 shown in FIG. 5 through FIG. 10 may include the plurality of light sources 170, at least one of which may emit light for sterilization. Accordingly, in the adhesive-type insect trap 3000, 4000, 5000, 6000, 7000 or 8000 according to the embodiments of the disclosure, a light source for sterilization is disposed to emit UVC light towards the adhesive sheet 140, 240, 340 or 440 and the interior of the adhesive-type insect trap 3000, 4000, 5000, 6000, 7000 or 8000, thereby rapidly killing insects and sterilizing or neutralizing bacteria contained in the insects or generated within the adhesive-type insect trap 3000, 4000, 5000, 6000, 7000 or 8000. In FIG. 5 through FIG. 10, the plurality of light sources 170 is described for convenience of explanation, but different light sources may be used based on different arrangements of a reflector, an adhesive sheet, or other parts of the adhesive-type insect traps.

Figure 11:
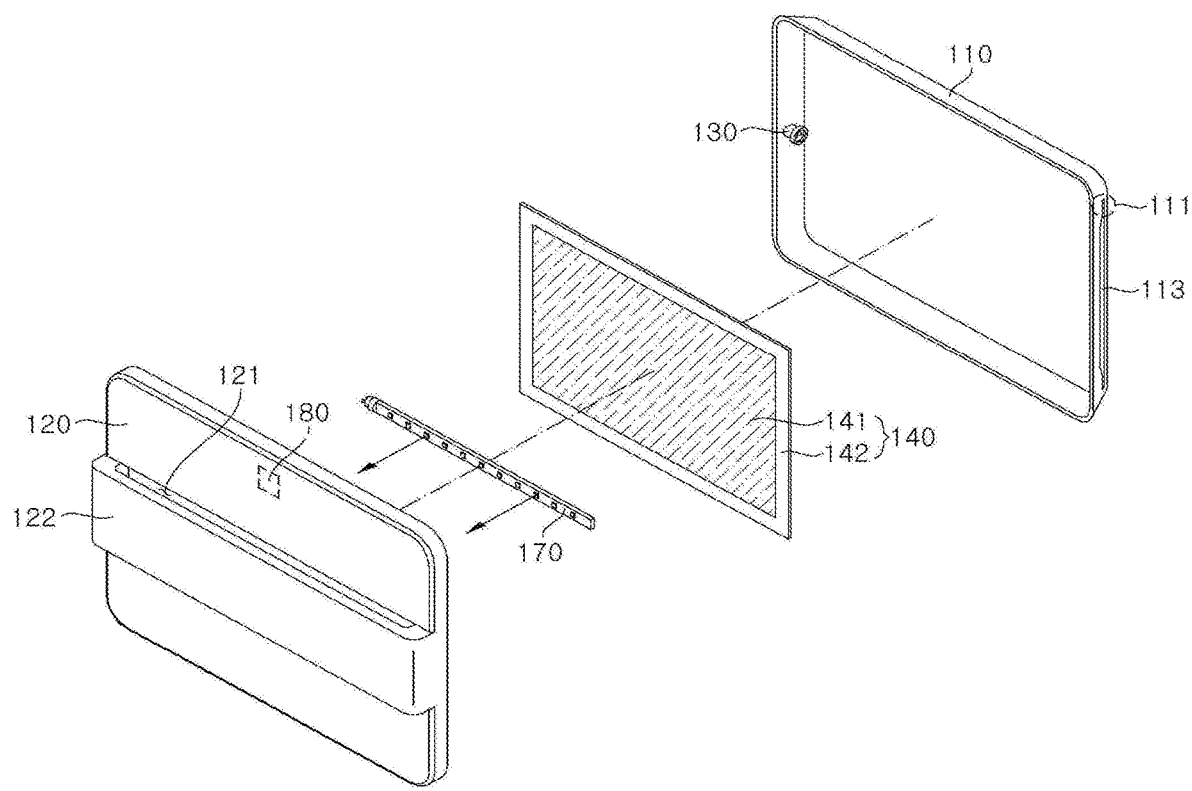
FIG. 11 shows an adhesive-type insect trap having a sensor according to an embodiment of the present disclosure.

Referring to FIG. 11, an adhesive-type insect trap 9000 may further include a sensor 180. The sensor 180 may detect at least one of the kind of insect trapped on the adhesive sheet 140, an area of the adhesive sheet 140 trapping insects, brightness of the adhesive sheet 140, an ambient temperature of the light source 170, intensity of light emitted from the light source 170, ambient illuminance of the insect trap 9000, insertion of the adhesive sheet 140 into the insect trap, and attachment of the cover 120 to the insect trap 9000.

In one embodiment, the sensor 180 may include a UV sensor capable of detecting the intensity of light emitted from the light source 170 to display an alarm message to a user before lifespan of the light source 170 is finished. The alarm message may be displayed through a separate lamp (not shown) or a separate sound generator (not shown) mounted on the adhesive-type insect trap 9000.

In another embodiment, the sensor 180 may include an illuminance sensor capable of detecting illuminance of surrounding light around the adhesive-type insect trap 9000. For example, the illuminance sensor may be set to have at least one preset illuminance range of the surrounding light and the intensity of light emitted from the light source 170 may be automatically controlled depending upon the illuminance range of the surrounding light. In addition, the adhesive-type insect trap 9000 may further include a luminous intensity regulator (not shown) for regulation of the luminous intensity of the light source 170 to display a desirable luminous intensity of the light source 170 depending upon the illuminance range such that a user can manually regulate the luminous intensity. That is, the adhesive-type insect trap 9000 controls the light source 170 to emit light having suitable intensity for insect attraction, thereby enabling efficient power consumption.

In a further embodiment, the adhesive-type insect trap 9000 may further include a temperature sensor (not shown). The temperature sensor may detect heat generated from the light source 170 mounted on the adhesive-type insect trap 9000 to stop power supply to the light source 170 when the temperature increases above a preset temperature.

In yet another embodiment, the adhesive-type insect trap 9000 may include a magnetic sensor for detecting whether the adhesive sheet 140 is inserted into the main body and whether the cover 120 is attached thereto to display an alarm message to a user when the adhesive sheet 140 is incompletely inserted or the cover 120 is incompletely attached to the main body 110.

In yet another embodiment, the adhesive-type insect trap 9000 may include a limit sensor. The limit sensor may permit power supply to the light source 170 when the adhesive sheet 140 is inserted into the main body 110 or the cover 120 is attached to the main body 110, and may stop power supply to the light source or display an alarm message to a user, as described above, when the adhesive sheet 140 is incompletely inserted or the cover 120 is incompletely attached to the main body 110.

In yet another embodiment, the adhesive-type insect trap 9000 may include a photosensor for detecting inflow of insects into the main body. When the insects enter the adhesive-type insect trap 9000, the photosensor may indicate an alarm message to a user, as described above, or supply power to a camera configured to observe insects trapped therein, described below.

Figure 12:
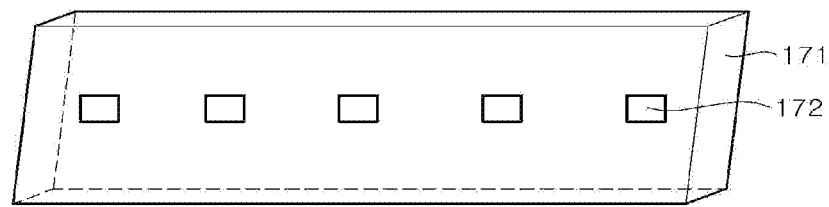
FIG. 12 shows a light source having a single support member according to an embodiment of the present disclosure.
Figure 13:
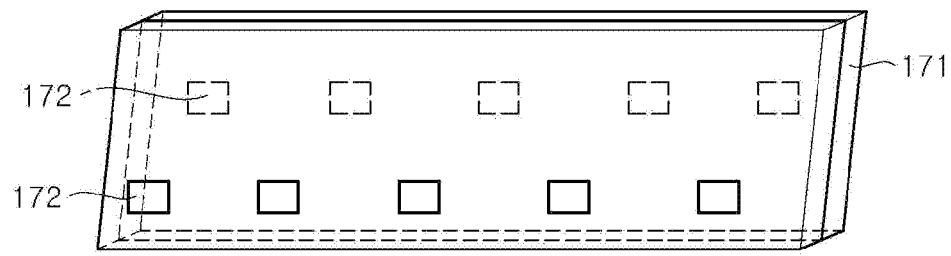
FIG. 13 shows a light source having a stack of support members according to an embodiment of the present disclosure.
Figure 14:
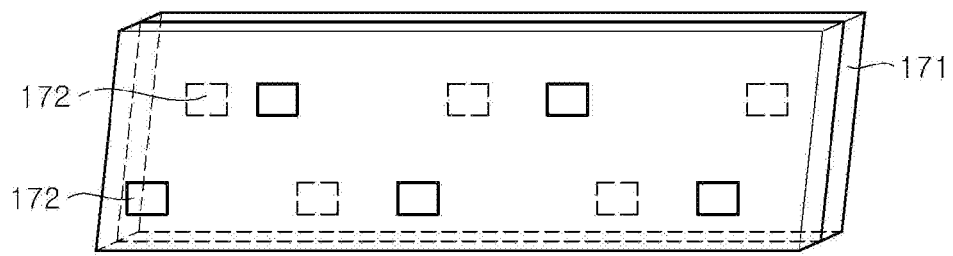
FIG. 14 shows a light source having a different arrangement of light emitting diodes from FIG. 13 according to an embodiment of the present disclosure.
Figure 15:
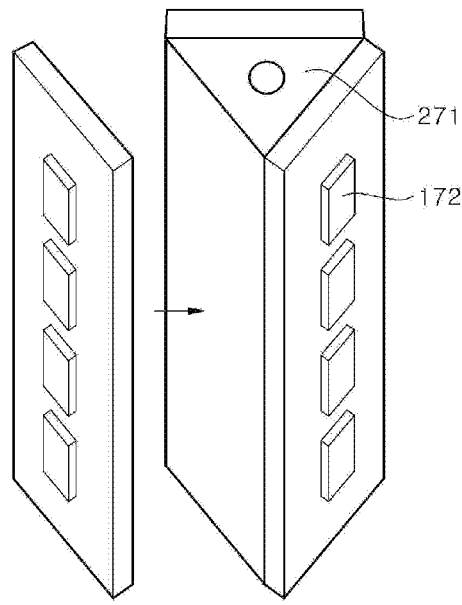
FIG. 15 shows a light source mounted on a polygonal column-shaped support member according to an embodiment of the present disclosure.
Figure 16:
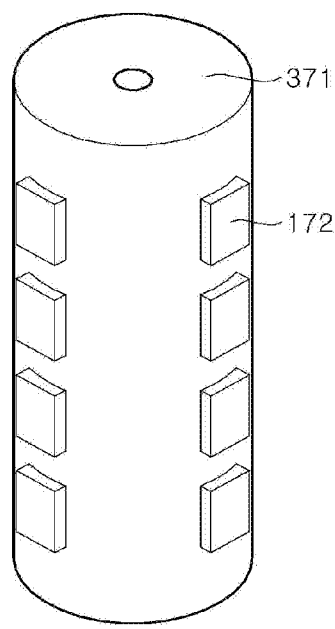
FIG. 16 shows a light source mounted on a cylindrical support member according to an embodiment of the present disclosure.
Figure 17:
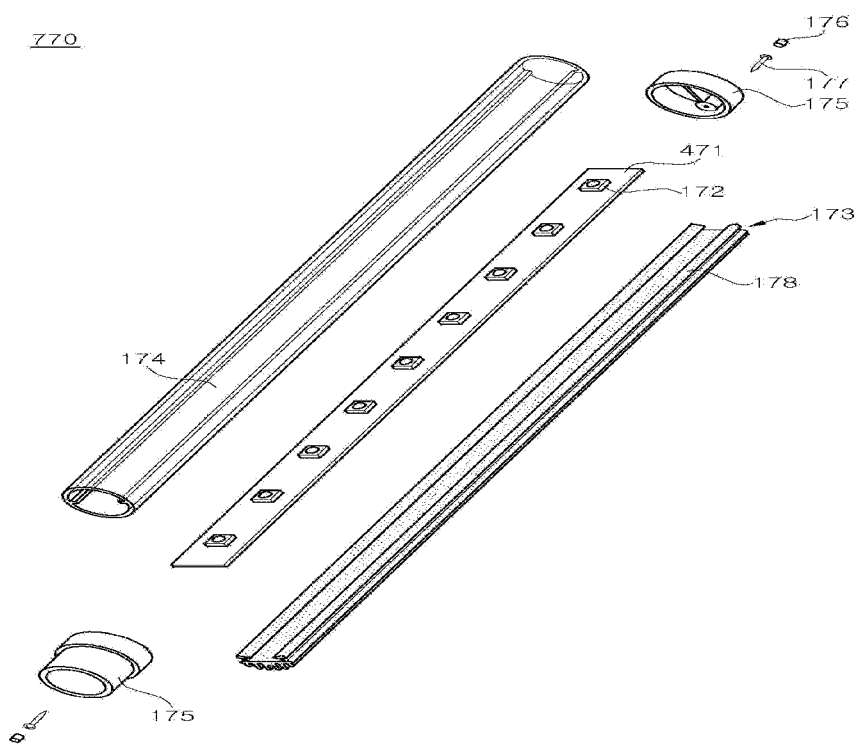
FIG. 17 shows a light source according to an embodiment of the present disclosure.

FIG. 12 through FIG. 17 show various embodiments of light sources 170, 270, 370, 470, 570, 670, 770 mounted on the light source mount 130 of the adhesive-type insect trap 2000, 3000, 4000, 5000, 6000, 7000, 8000 or 9000. FIG. 12 shows a light source having a single support member according to an embodiment of the present disclosure. FIG. 13 shows a light source having a stack of support members according to an embodiment of the present disclosure. FIG. 14 shows a light source having a different arrangement of light emitting diodes from FIG. 13 according to an embodiment of the present disclosure. FIG. 15 shows a light source mounted on a polygonal column-shaped support member according to an embodiment of the present disclosure. FIG. 16 shows a light source mounted on a cylindrical support member according to an embodiment of the present disclosure. FIG. 17 shows a light source according to an embodiment of the present disclosure.

The light source 170, 270, 370, 470, 570, 670 or 770 may include light emitting diodes 172 attached to a support member 171, 271, 371 or 471. As shown in FIG. 12 to FIG. 16, the light source 170, 270, 370, 470, 570, 670 or 770 may include a single support member 171 or a stack of support members 171. On the stack of support members 171, the light emitting diodes 172 are disposed in a zigzag arrangement to suppress damage to the support members by heat therefrom.

Referring to FIG. 15 and FIG. 16, the light source 570 or 670 includes the light emitting diodes 172 mounted on a polygonal column-shaped support member 570 or a cylindrical support member 670 to reduce the volume of the adhesive-type insect trap 2000, 3000, 4000, 5000, 6000, 7000, 8000 or 9000 while allowing emission of light in a broad range, thereby improving light irradiation efficiency. By way of example, a triangular support member 570 may be formed by coupling three PCBs in a triangular shape.

In another embodiment, the support member may include a flexible support member. The flexible support member may be entirely or partially bendable. That is, in order to reduce the size of the adhesive-type insect trap 2000, 3000, 4000, 5000, 6000, 7000, 8000 or 9000 according to the embodiments of the disclosure while improving insect attraction efficiency, the light source mount may have a bent shape or may be bendable and the flexible support member may be mounted on a light source mount (not shown) having a bent shape or on a light source mount (not shown) deformed in a bent shape.

Referring to FIG. 17, the light source 770 may be a tube type LED. The tube type LED 770 may be electrically connected to an external power supply via wire bonding or without wire bonding. By way of example, the tube type LED 770 has a structure in which light emitting diodes 172 are attached to a support member 471 mounted on one surface of a heat sink 173, and includes a case 174 receiving the support member 471 and the heat sink 173 therein and bases 175 coupled to opposite sides of the case 174. By way of example, the heat sink 173 may further include a support member holder 178 surrounding both sides of the support member 471. At least one surface of the support member holder 178 has a gradually increasing height from an inner side thereof, on which the support member 471 is seated, towards an outer periphery thereof. By way of example, the aforementioned support member 171, 271 or 371 may be mounted on the tube type LED 770. By way of example, the tube type LED 770 may include light emitting diodes 172 attached to both sides of the support member 171 or 471, in which light emitting diodes for insect attraction are attached to one side of the support member and UVC light emitting diodes for sterilization and killing of insects are attached to the other side thereof.

Figure 18:
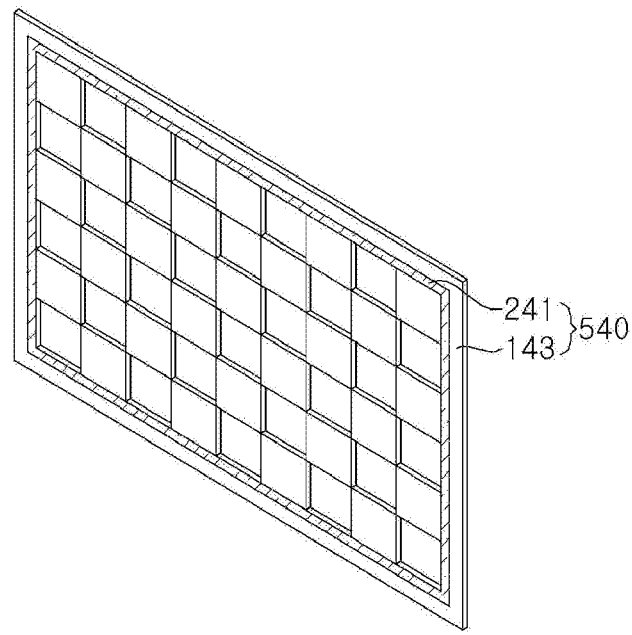
FIG. 18 shows an adhesive sheet including a flypaper piece and a reflective sheet according to embodiments of the present disclosure.

Referring to FIG. 18, in the adhesive-type insect trap 1000, 2000, 3000, 4000, 5000, 6000, 7000, 8000 or 9000, an adhesive sheet 540 includes flypaper pieces 141, 241 and a reflective sheet 143. The reflective sheet 143 may refer to a member on which the flypaper piece 141, 241 are deposited or coated. Here, the flypaper piece 141 may be formed of a light transmissive material to allow light emitted from the light source to pass therethrough and the flypaper piece 241 may include an opaque material. In this case, the flypaper piece 241 may be disposed in a lattice shape on the reflective sheet 143 such that light emitted from the light source 170 is reflected by the reflective sheet 143 to attract insects. That is, the adhesive-type insect trap 1000, 2000, 3000, 4000, 5000, 6000, 7000, 8000 or 9000 may allow light emitted from the light source 170, 270, 370, 470, 570, 670 or 770 to be reflected by the reflective sheet 143 such that the cover 120 can be irradiated in a large area with the light when the light passes through the cover 120, and may guide insects collected in the adhesive-type insect trap 1000, 2000, 3000, 4000, 5000, 6000, 7000, 8000 or 9000 by the reflected light to remain inside the main body 110, thereby improving insect trapping efficiency. Insects, particularly flies, tend to be more strongly attracted to refracted or diffused light than to direct light. Thus, the adhesive-type insect trap 1000, 2000, 3000, 4000, 5000, 6000, 7000, 8000 or 9000 allow light emitted from the light source 170 to be reflected at least once by the reflective sheet 143 instead of directly passing through the cover, thereby improving insect attraction efficiency with decoy light.

Figure 19:
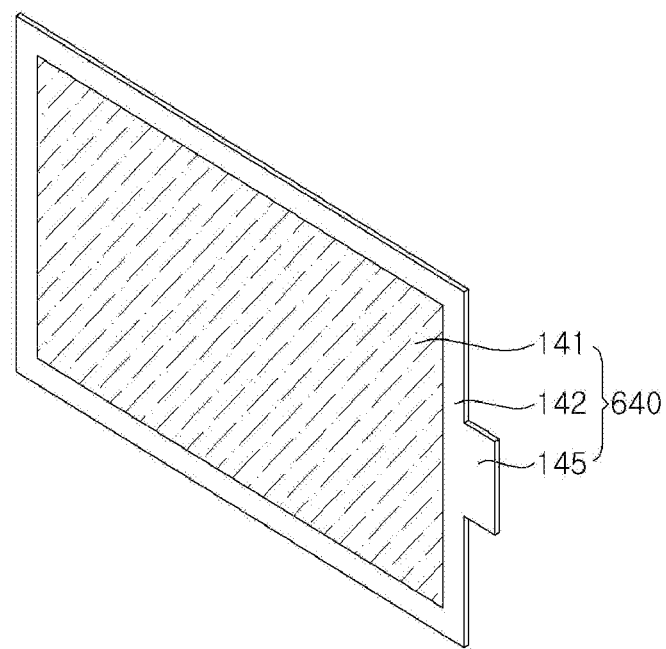
FIG. 19 shows an adhesive sheet including a gripper according to embodiments of the present disclosure.

Referring to FIG. 19, an adhesive sheet 640 includes a gripper 145, which extends a preset length therefrom to allow a user to easily grip the gripper 145 upon insertion or separation of the adhesive sheet 640 into or from the adhesive-type insect trap 1000, 2000, 3000, 4000, 5000, 6000, 7000, 8000 or 9000 in a vertical direction or in a horizontal direction. Accordingly, the adhesive sheet 640 may be provided to the adhesive-type insect trap by inserting the adhesive sheet 140 into a space between the main body 110 and the guide groove 111 in a downward direction or in a leftward direction using the gripper 145, and may be replaced by separating the adhesive sheet 640 therefrom in an upward direction or in a rightward direction using the gripper 145.

Figure 20:
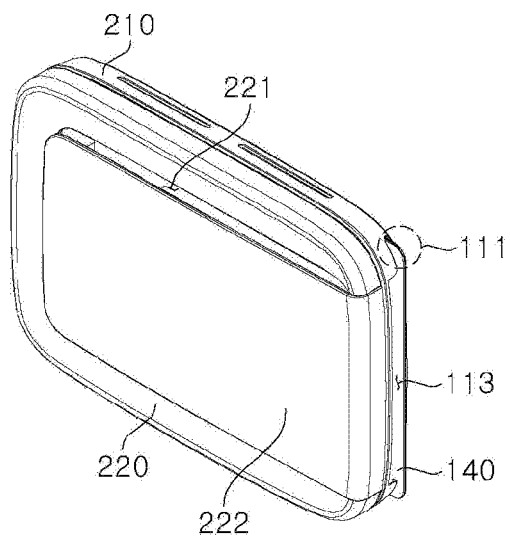
FIG. 20 shows an adhesive-type insect trap having a cover with a through-hole blocking structure according to an embodiment of the present disclosure.
Figure 21:
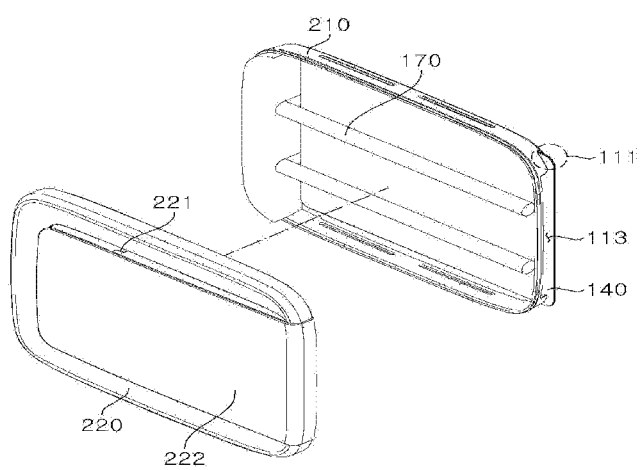
FIG. 21 shows a dissembled state of the adhesive-type insect trap of FIG. 21 according to an embodiment of the present disclosure.
Figure 22:
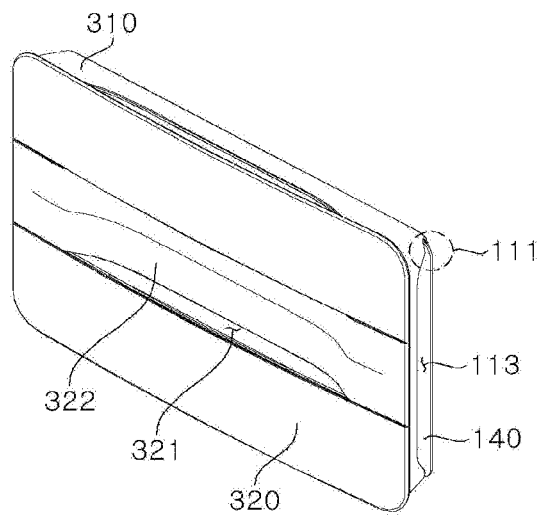
FIG. 22 shows an adhesive-type insect trap showing a cover having a concavely depressed through-hole according to an embodiment of the present disclosure.
Figure 23:
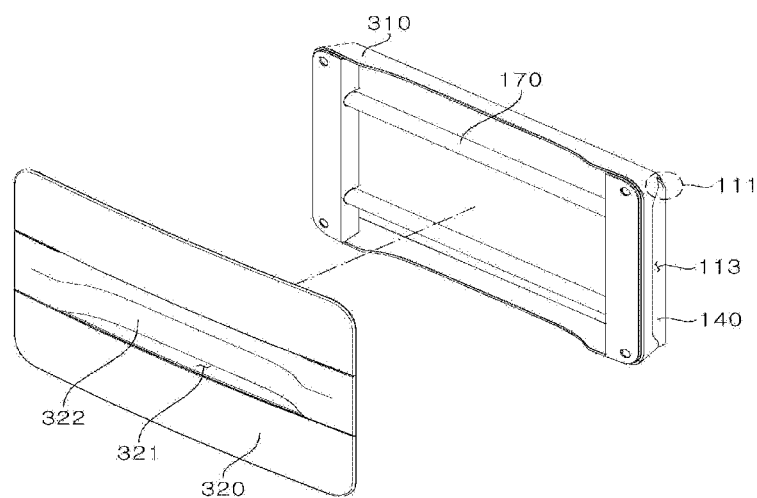
FIG. 23 shows a dissembled state of the adhesive-type insect trap of FIG. 22 according to an embodiment of the present disclosure.

Referring to FIG. 20 to FIG. 23, adhesive-type insect traps 1100, 1200 may adopt the structure of the adhesive-type insect trap 1000, 2000, 3000, 4000, 5000, 6000, 7000, 8000 or 9000, and the following description will focus on various embodiments of covers 220, 320. FIG. 20 shows an adhesive-type insect trap having a cover with a through-hole blocking structure according to an embodiment of the present disclosure. FIG. 21 shows a dissembled state of the adhesive-type insect trap of FIG. 21 according to an embodiment of the present disclosure. FIG. 22 shows an adhesive-type insect trap showing a cover having a concavely depressed through-hole according to an embodiment of the present disclosure. FIG. 23 shows a dissembled state of the adhesive-type insect trap of FIG. 22 according to an embodiment of the present disclosure.

Referring to FIG. 20 and FIG. 21, in the adhesive-type insect trap 1100, the cover 220 may include a through-hole blocking structure 222 adapted to block at least a portion of a through-hole 221, which may be depressed into the cover 220. For example, the through-hole blocking structure 222 may extend from an edge of the cover 220 in a horizontal direction of the cover 220. That is, the adhesive-type insect trap 1100 is configured to maximize the area of the through-hole 221 to improve insect trapping efficiency and to prevent the through-hole blocking structure 222 from protruding from the cover 220 so as to reduce the volume thereof, thereby enabling miniaturization thereof.

Referring to FIG. 22 and FIG. 23, in the adhesive-type insect trap 1200, the cover 320 may include a through-hole blocking structure 322 adapted to block at least a portion of a through-hole 321, which is concavely depressed into the cover 320. For example, the through-hole blocking structure 322 may be integrally formed with the cover 320 and the through-hole 321 may include a step of the cover 320 formed by the concave shape of the through-hole blocking structure 322. That is, in the adhesive-type insect trap 1200, the through-hole blocking structure 322 prevents the adhesive sheet 140 from being viewed through the through-hole 321 from the outside so as to prevent insects attached to the adhesive sheet 140, 240, 340, 440, 540 or 640 from being observed from the outside and does not protrude outwards from the cover 320, thereby enabling miniaturization of the adhesive-type insect trap 1200.

Figure 24:
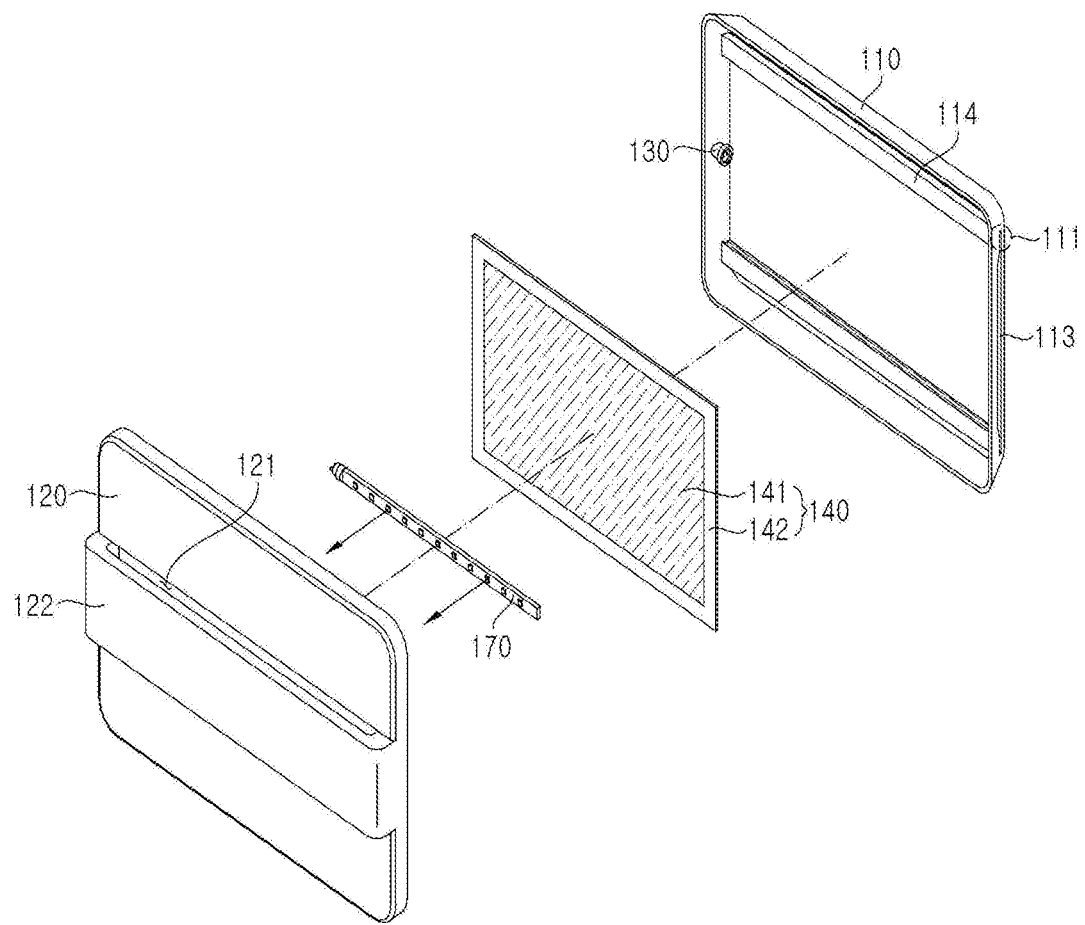
FIG. 24 shows an adhesive-type insect trap having a main body with a guide rail according to an embodiment of the present disclosure.

Referring to FIG. 24, in the adhesive-type insect trap 1000, 2000, 3000, 4000, 5000, 6000, 7000, 8000, 9000, 1100 or 1200, the main body 110 may have a guide rail 114 which guides the adhesive sheet 140, 240, 340, 440, 540 or 640 into the main body 110. The guide rail 114 may guide the adhesive sheet 140, 240, 340, 440, 540 or 640 to be secured inserted into the main body 110 along the guide groove 111 or 211 without being adhered to the main body 110. Further, the guide rail 114 may have a thickness corresponding to a thickness of the adhesive sheet 140, 240, 340, 440, 540 or 640 to allow easy insertion and separation of the adhesive sheet 140, 240, 340, 440, 540 or 640 while receiving an edge of the adhesive sheet 140, 240, 340, 440, 540 or 640 inserted thereinto, and a depth preventing the flypaper piece 141 of the adhesive sheet 140, 240, 340, 440, 540 or 640 from contacting the main body 110.

Figure 25:
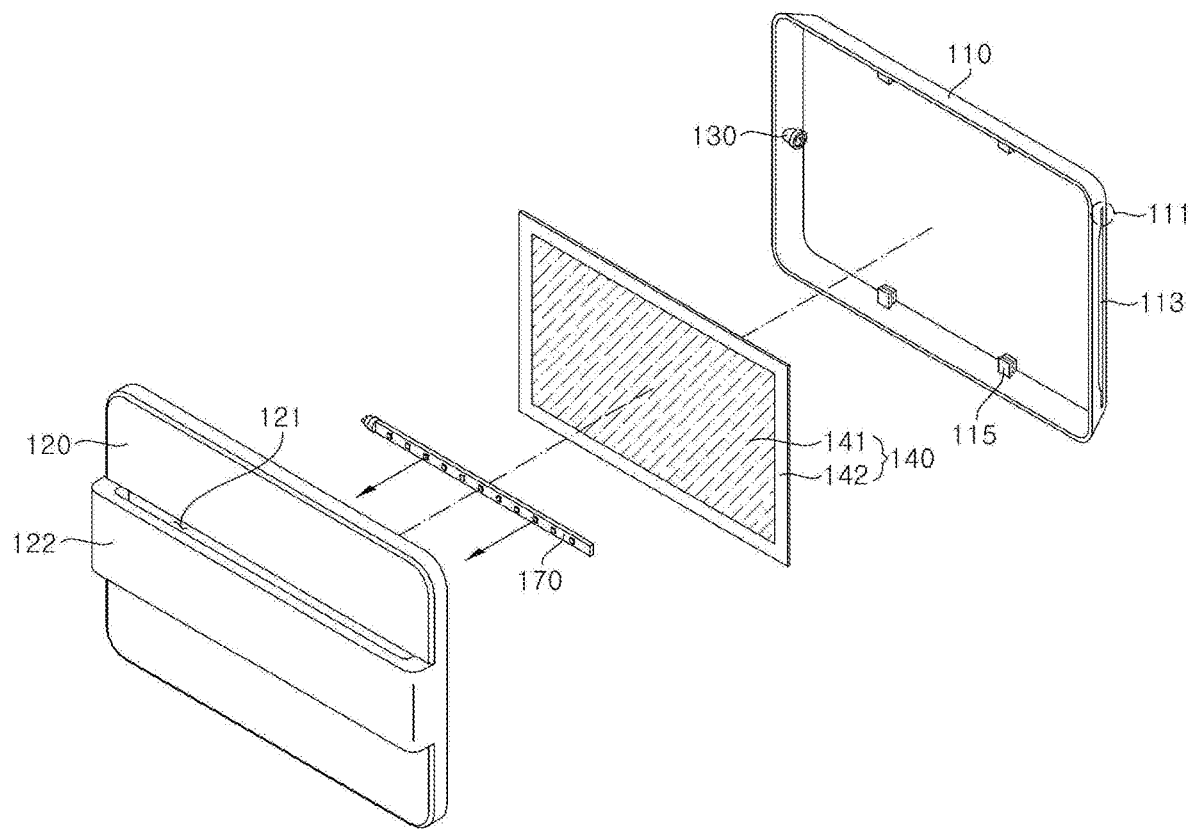
FIG. 25 shows an adhesive-type insect trap having a main body with one exemplary adhesive sheet support according to an embodiment of the present disclosure.
Figure 26:
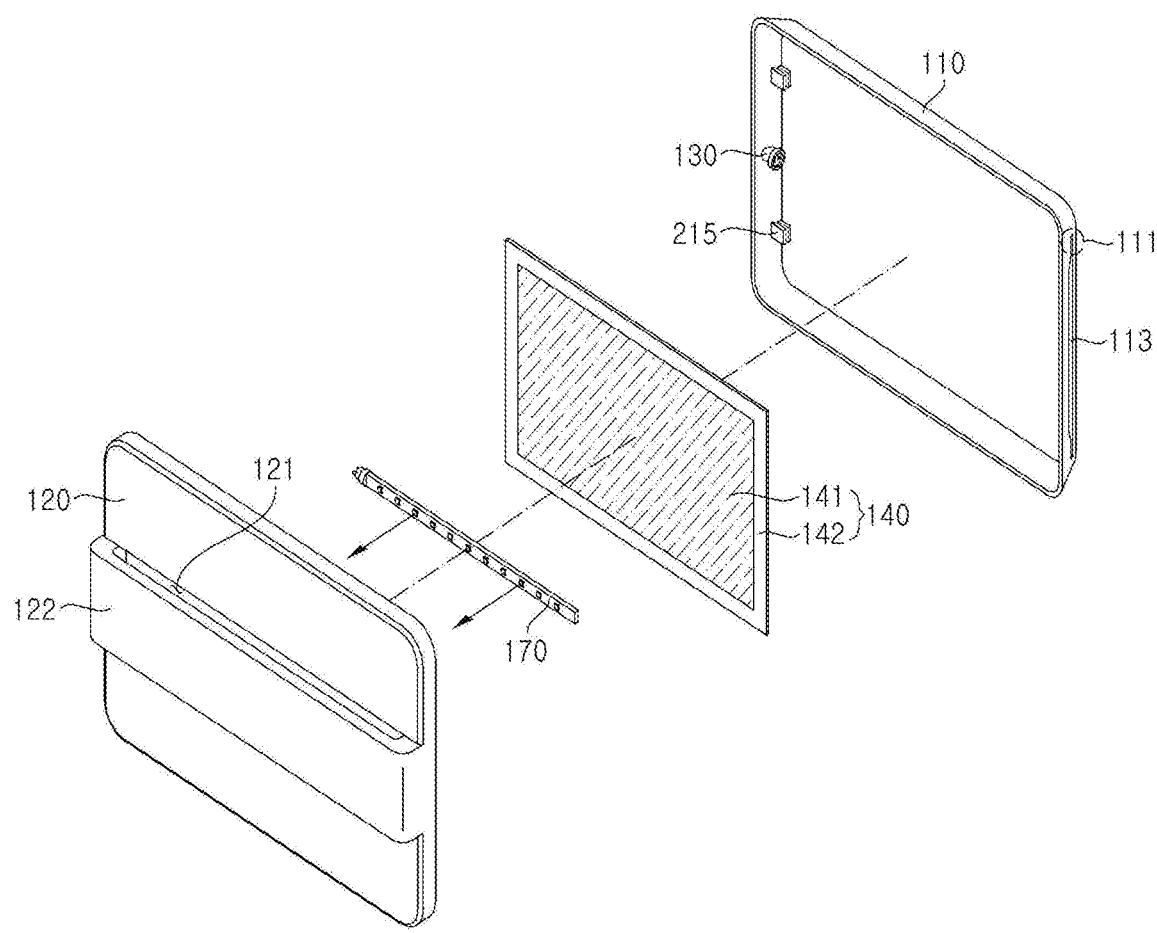
FIG. 26 shows an adhesive-type insect trap having a main body with another exemplary adhesive sheet support according to an embodiment of the present disclosure.

Referring to FIG. 25 and FIG. 26, in the adhesive-type insect trap 1000, 2000, 3000, 4000, 5000, 6000, 7000, 8000, 9000, 1100 or 1200, the main body 110 may be provided with an adhesive sheet support 115 or 215. The adhesive sheet support 115 or 215 may support or secure the adhesive sheet 140, 240, 340, 440, 540 or 640 to prevent the adhesive sheet 140, 240, 340, 440, 540 or 640 inserted into the main body 110 from being adhered to the main body 110.

Figure 27:
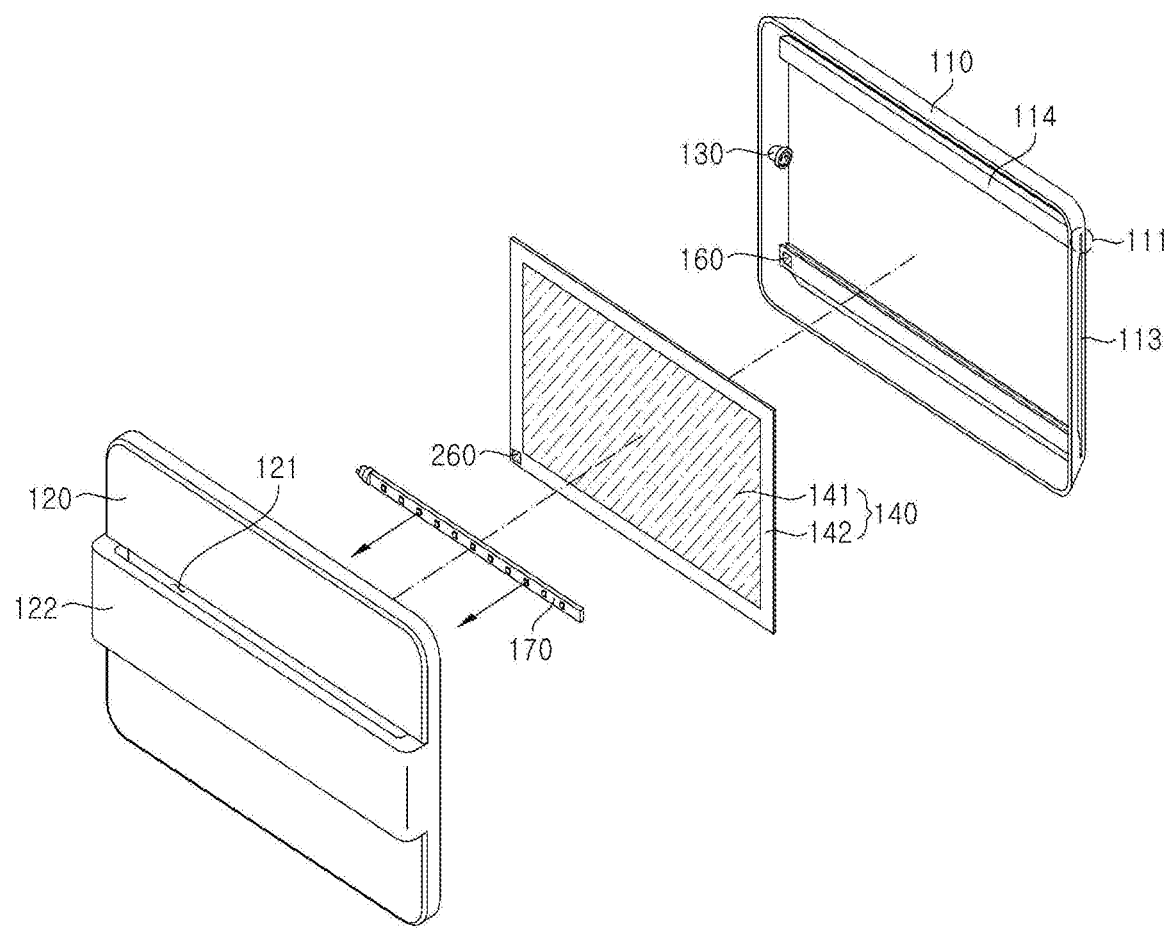
FIG. 27 shows an adhesive-type insect trap having magnet members according to an embodiment of the present disclosure.

Referring to FIG. 27, in the adhesive-type insect trap 1000, 2000, 3000, 4000, 5000, 6000, 7000, 8000, 9000, 1100 or 1200, the guide rail 114 and the adhesive sheet 140, 240, 340, 440, 540 or 640 may include magnet members 160, 260 disposed to face each other and having opposite polarities. That is, the adhesive sheet 140, 240, 340, 440, 540 or 640 are prevented from being separated from the main body even upon rotation of the adhesive-type insect trap 1000, 2000, 3000, 4000, 5000, 6000, 7000, 8000, 9000, 1100 or 1200 according to installation environments by a user after the adhesive sheet 140, 240, 340, 440, 540 or 640 is inserted into the main body 110.

The adhesive-type insect trap 1000, 2000, 3000, 4000, 5000, 6000, 7000, 8000, 9000, 1100 or 1200 may further include a photocatalyst. For example, the photocatalyst may be coated or attached to the rear side of the cover 120, the front side or the lateral side of the main body 110, the reflector 150 or 250, and the adhesive sheet 140, 240, 340 or 440. Alternatively, a separate photocatalyst filter may be mounted on the adhesive-type insect traps.

The photocatalyst may include photocatalyst media generating photocatalytic reaction. For example, the photocatalyst media may include titanium oxide ($TiO_2$), silicon oxide ($SiO_2$), tungsten oxide ($WO_3$), zirconium oxide (ZnO), strontium titanium oxide ($SrTiO_3$), niobium oxide ($Nb_2O_5$), iron oxide ($Fe_2O_3$), zinc oxide ($ZnO_2$), tin oxide ($SnO_2$), and the like.

In addition, hydroxyl radicals generated by photocatalytic reaction of the photocatalyst act as a strong oxidant, which performs a sterilization function, and decomposes contaminants and odorous substances in air, which has flown into the adhesive-type insect trap 1000, 2000, 3000, 4000, 5000, 6000, 7000, 8000, 9000, 1100 or 1200, into water and carbon dioxide by decomposing organic contaminants in air through oxidation. Here, carbon dioxide is known as a substance having an effect of attracting mosquitoes.

As such, the adhesive-type insect trap 1000, 2000, 3000, 4000, 5000, 6000, 7000, 8000, 9000, 1100 or 1200 further include the photocatalyst to provide not only sterilization and deodorization effects, but also an effect of attracting insects, particularly mosquitoes, through generation of carbon dioxide during photocatalytic reaction.

The adhesive-type insect trap 1000, 2000, 3000, 4000, 5000, 6000, 7000, 8000, 9000, 1100 or 1200 may further include a switch (not shown) for controlling a power supply system of the light source mount 130. Here, a power supply may be disposed at any location without being limited to a particular location.

Further, the adhesive-type insect trap 1000, 2000, 3000, 4000, 5000, 6000, 7000, 8000, 9000, 1100 or 1200 may be provided with a sensor to allow a user to determine the presence of insects collected in the insect traps or an area occupied by insects collected on the adhesive sheet 140, 240, 340 or 440, and may perform a notification function to a user through the communication module when the presence of insects collected in the insect trap is detected by the sensor or when the area occupied by the insects exceeds a preset value. By way of example, the sensor may include a brightness sensor for detecting brightness of the adhesive sheet 140, 240, 340 or 440. The brightness sensor may detect a collected amount of insects through brightness comparison between a region to which insects are attached and a region to which no insects are attached.

Further, the adhesive-type insect trap 1000, 2000, 3000, 4000, 5000, 6000, 7000, 8000, 9000, 1100 or 1200 may include an insect attractant spray (not shown) or may include an insect attractant contained in an adhesive sheet to improve insect attraction efficiency.

Further, the adhesive-type insect trap 1000, 2000, 3000, 4000, 5000, 6000, 7000, 8000, 9000, 1100 or 1200 may include a light diffusion material applied to or coated on the adhesive sheet 140, 240, 340 or 440 to diffuse light emitted from the light source 170, 270, 370, 470, 570, 670 or 770, thereby improving efficiency in attraction of insects, particularly flies.

Insects, particularly flies, tend to be more strongly attracted to refracted or diffused light than to direct light. The adhesive-type insect trap 1000, 2000, 3000, 4000, 5000, 6000, 7000, 8000, 9000, 1100 or 1200 can refract or diffuse light emitted from the light source 170, 270, 370, 470, 570, 670 or 770, thereby improving efficiency in attraction of insects with decoy light. By way of example, the cover 120, 220 or 320 may have a roughened surface, may include a separate diffusion film attached thereto or coated thereon, or may include a diffusion agent applied thereto or coated thereon, wherein the surface of the cover 120, 220 or 320 includes outer and inner surfaces of the cover 120, 220 or 320. Alternatively, the reflector 150 or 250 may be a roughened surface, may include a separate diffusion film attached thereto or coated thereon, or may include a diffusion agent applied thereto or coated thereon. Alternatively, the light source 170, 270, 370, 470, 570, 670 or 770 may have a roughened surface, may include a separate diffusion film attached thereto or coated thereon, or may include a diffusion agent applied thereto or coated thereon. By way of example, the case 174 of the light source 770 shown in FIG. 17 may have a roughened surface, may be provided or coated with a separate diffusion film, may be coated with a diffusion agent, or may have a diffusion agent deposited thereon.

Referring to FIG. 28 to FIG. 33, adhesive-type insect traps described below have a structure to allow the light source 170, 270, 370, 470, 570, 670, 770 or 870 of the adhesive-type insect trap 1000, 2000, 3000, 4000, 5000, 6000, 7000, 8000, 9000, 1100 or 1200 to be stably inserted thereinto or secured thereto. In a typical insect trap configured to collect insects, such as flies, with decoy light, a light source is disposed to emit decoy light in a horizontal direction with respect to the ground in order to improve insect attraction efficiency. In such a typical adhesive-type insect trap, the light source is not stably installed or secured and thus can be separated from a light source installation unit due to the weight thereof or continuous impact from insects including flies, thereby deteriorating insect attraction efficiency with decoy light. In addition, upon application of excessive force upon installation or separation of the light source in the typical adhesive-type insect trap, insects can be separated from the adhesive sheet towards the bottom of the insect trap and decay to generate an unpleasant odor, thereby causing user inconvenience and deterioration in insect attraction efficiency. Accordingly, the inventors of the present disclosure performed numerous experiment for development of an installation structure of a light source 870, which allows the light source 870 to be stably installed and secured in a main body 410 and does not require excessive force upon separation and installation of the light source, thereby completing the following configuration.

Figure 28:
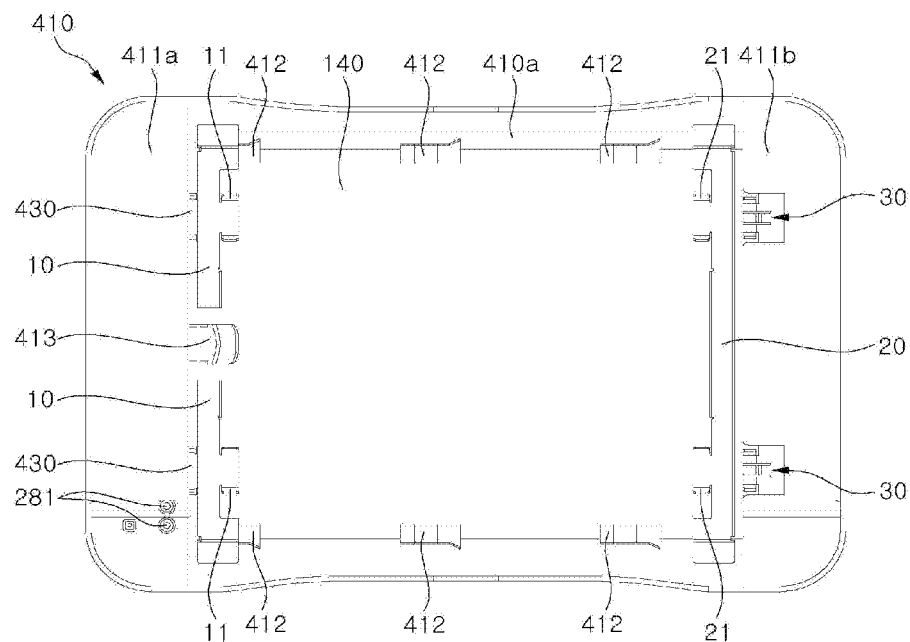
FIG. 28 shows the adhesive-type insect traps according to the embodiments of the present disclosure, with a cover separated from a main body thereof.
Figure 29:
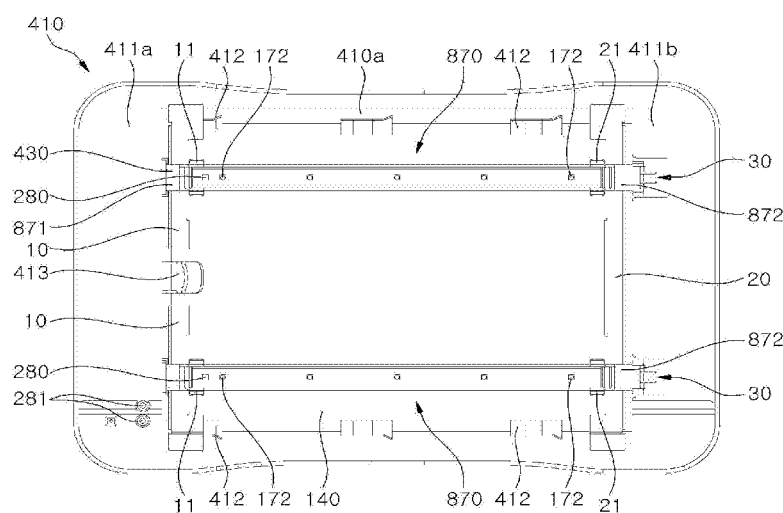
FIG. 29 shows a light source included in the adhesive insect trap as shown in FIG. 28.

FIG. 28 and FIG. 29 show the adhesive-type insect traps according to the embodiment of the present disclosure, with a cover separated from a main body thereof, in which FIG. 29 shows the adhesive insect trap further including a light source 870 in the adhesive-type insect trap of FIG. 28.

Referring to FIG. 28 and FIG. 29, the main body 410 of the adhesive-type insect trap includes a main body bottom 410a, side portions 411a, 411b, a light source mount 430, a light source seat 30, a pressing member 31, a securing member 32, light source support members 10, 20, and light source-pressing members 11, 21.

The main body bottom 410a refers to a region in which the adhesive sheet 140, 240, 340, 440, 540 or 640 is inserted into the main body and disposed at an upper side thereof, the side portions 411a, 411b are disposed at both sides thereof, and the guide member 412 and the stopper unit 413 are disposed.

The side portions 411a, 411b may contact the side surfaces of the main body 410 or may be separated by a predetermined distance from the main body 410. For example, the side portions may be disposed to contact the side surfaces of the main body 410 to allow efficient use of a space defined in the main body 410. The side portions 411 may be provided with circuits (not shown) and a power supply (not shown), which supplies power to the light source 870, the sensor 280, a display unit 281, and the like, and may include a separate housing to prevent damage to the power supply and the circuit due to intrusion of insects or dust. The side portions 411*a*, 411*b* may be further provided with the sensor 280 and the display unit 281. Here, the sensor 280 may include a sensor 290 for detecting, for example, at least one of the kind of insect trapped on the adhesive sheet 140, 240, 340, 440, 540 or 640, an area of the adhesive sheet 140, 240, 340, 440, 540 or 640 trapping insects, brightness of the adhesive sheet 140, 240, 340, 440, 540 or 640, an ambient temperature of the light source 870, the intensity of light emitted from the light source 870, illuminance of ambient light around the adhesive-type insect trap, insertion of the adhesive sheet 140, 240, 340, 440, 540 or 640 into the insect trap, and attachment of the cover 120, 220, 320 to the insect trap, as described above. For example, the sensor 280 may include a UV sensor 280, an illuminance sensor, a temperature sensor, a magnetic sensor, a limit sensor, a photosensor, and the like.

The display unit 281 may emit indication light when data values detected by the sensor 280 are greater than or less than preset values. For example, when the intensity of light emitted from the light source 870 detected by the UV sensor 280 is less than a preset range, the display unit 281 may emit indication light, which may indicate a light source replacement signal. For example, when the ambient temperature around the light source 870 detected by the temperature sensor exceeds a preset range, the display unit 281 may emit indication light, which may indicate a warning signal of the light source 870. For example, when no insertion of the adhesive sheet 140, 240, 340, 440, 540 or 640 or incomplete attachment of the cover 120, 220 or 320 is detected by the magnetic sensor or the limit sensor, the display unit 281 may emit indication light, which may indicate a signal indicating incomplete preparation for operation.

The guide member 412 guides the adhesive sheet 140, 240, 340, 440, 540 or 640 to be stably inserted into the main body 410 and may be provided in plural. For example, the guide members 412 may be separated from each other by a predetermined distance. The stopper unit 413 allows the adhesive sheet 140, 240, 340, 440, 540 or 640 to be stably inserted into the main body 410 and secured thereto, and may be provided singularly or in plural. For example, the stopper unit may be disposed between the plural light source mounts 430 or between the plural light source support members 10, 20.

Figure 33A:
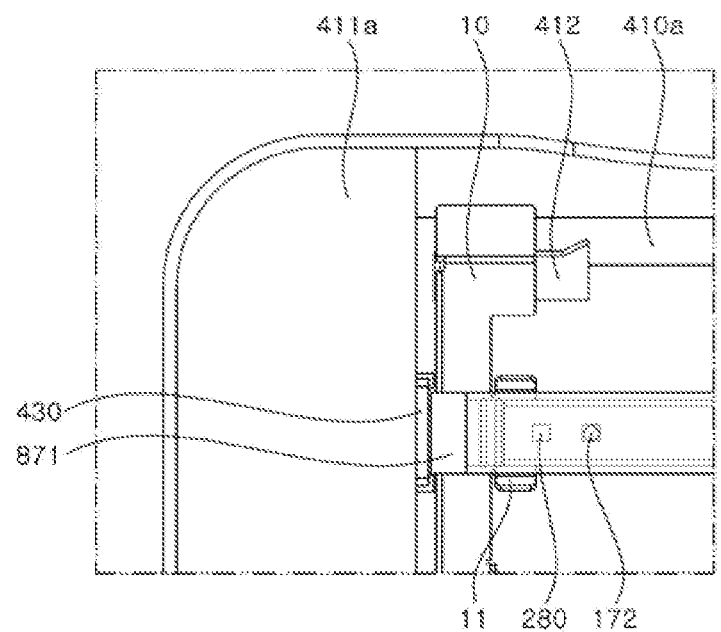
FIG. 33(a) shows a light source mounted on a light source mount according to one embodiment of the present disclosure.
Figure 33B:
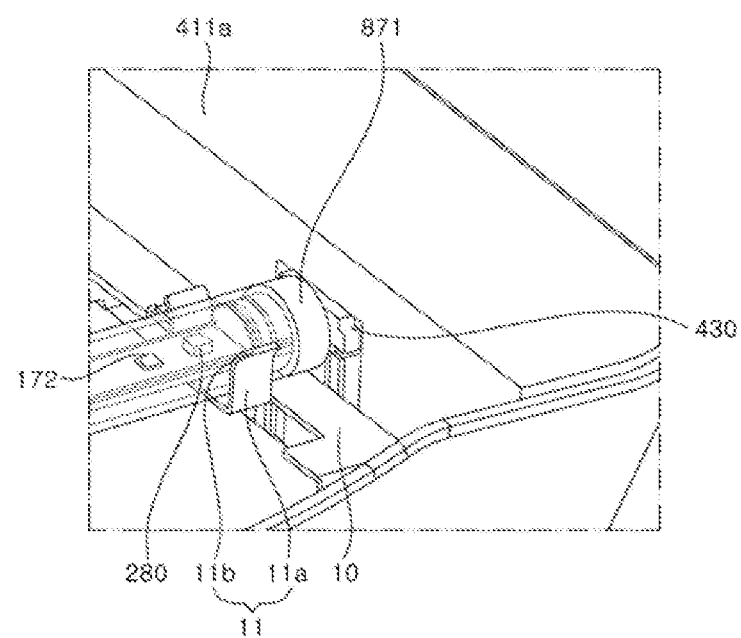
FIG. 33(b) shows a top perspective view of FIG. 33(b).

At least a portion of the light source mount 430 may be connected to the side portion 411*a*. For example, the light source mount 430 may be disposed outside the side portion 411*a* or inside the side portion 411*a*. For example, as shown in FIG. 29 and FIG. 33, a contact terminal of the light source 870 may be inserted into the light source mount 430 to receive power sent from a circuit disposed inside the side portion 411*a* such that the light source 870 can be operated by the power.

The light source seat 30 allows the light source 870 to be stably installed and secured in the insect trap, and may be disposed at a location in the main body 410 to face the light source mount 430. For example, the light source seat 30 is disposed on the side portion 411*b*, which is disposed to face the side portion 411*a* provided with the light source mount 430, such that one side of the light source 870 is mounted on the light source mount 430 and the other side of the light source 870 is seated on the light source seat 30. That is, in the adhesive-type insect trap according to the embodiments of the present disclosure, the light source 870 is stably installed and supported at both end thereof on the light source mount 430 and the light source seat 30, thereby improving insect collection efficiency while maintaining efficiency in attraction of insects including flies with decoy light in an optimal state.

Figure 30A:
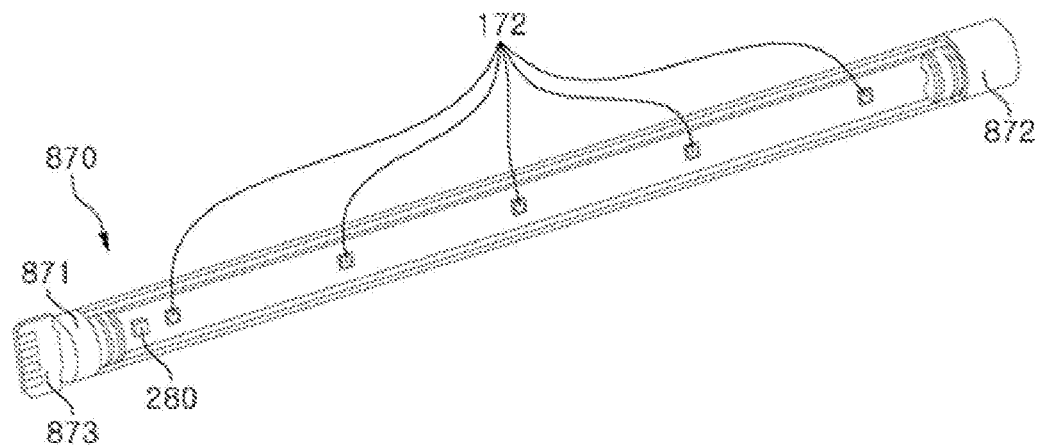
FIG. 30(a) shows a light source according to one embodiment of the present disclosure.
Figure 30B:
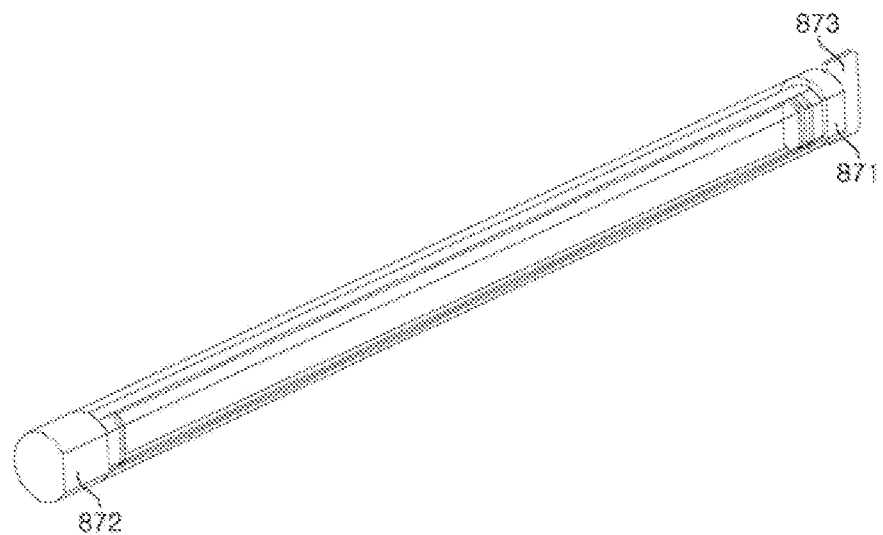
FIG. 30(b) shows the reverse side of FIG. 30(a).

FIG. 30 shows a light source according to one embodiment of the disclosure. Referring to FIG. 30, a light source 870 may include the same components as the light source 770 described with reference to FIG. 17 except for the UV sensor 280, a contact terminal 873, and end caps 871, 872.

As described above, the UV sensor 280 detects illuminance of light emitted from the light source 870 to send a signal indicating the illuminance of light to the controller such that lifespan of the light source 870 can be displayed through the display unit. For example, when the illuminance of light emitted from the light source 870 is less than a preset value, the display unit displays a signal for replacement of the light source 870 or the light emitting diode 172, thereby maintaining efficiency in attraction of insects including flies in an optimal state. The contact terminal 873 is provided with a circuit for supplying power to the light source 870 and is inserted into the light source mount 430 to receive power from the side portion 411*a*.

As shown in FIGS. 30 (*a*) and (*b*), the end caps 871, 872 are provided to opposite ends of a case (not shown) of the light source 870 corresponding to the case 174 of the light source 770 shown in FIG. 17, and serve to close the opposite ends of the case, which protects the light emitting diode from insects including flies, to prevent intrusion of external materials, thereby improving durability of the light source 870. Further, the end caps 871, 872 may be stably supported by the light source support members 10, 20 described below and may be stably disposed on the light source seat 30, as shown in FIG. 29. For example, the end cap 871 or 872 may include curved surfaces 872*a*, 872*b* and a planar surface 872*c* (FIG. 32), in which the curved surfaces 872*a*, 872*b* may have a constant radius of curvature or different radii of curvature. Details of the end cap will be described with reference to FIG. 31.

Figure 31A:
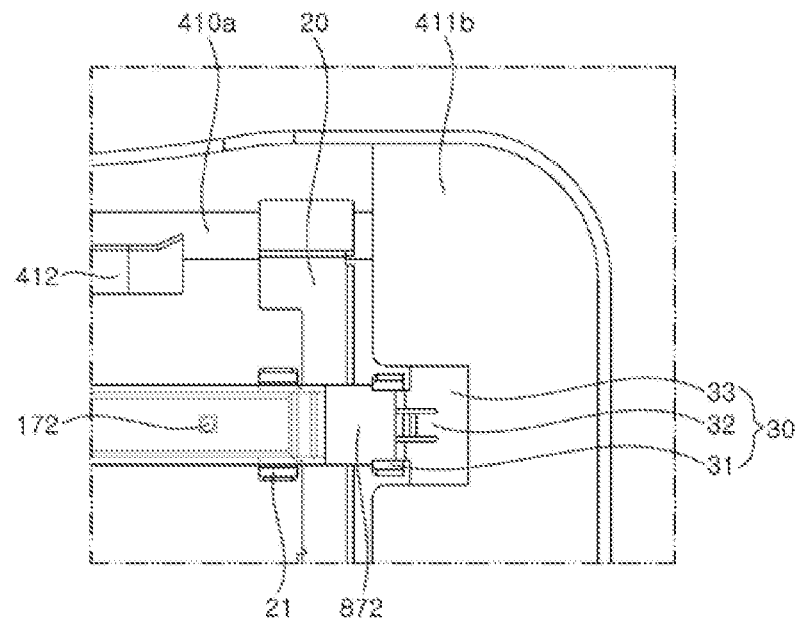
FIG. 31(a) shows the light source mounted on a light source seat according to one embodiment of the present disclosure.
Figure 31B:
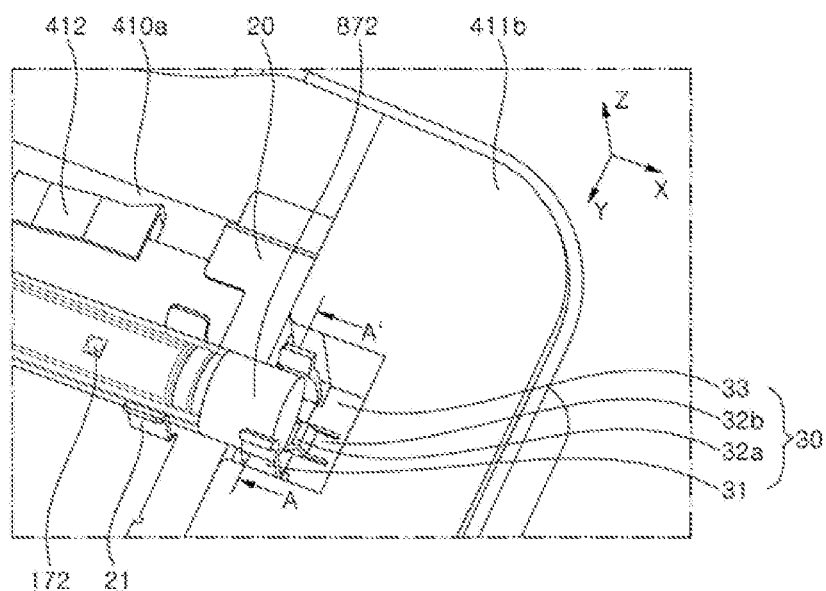
FIG. 31(b) shows a top perspective view of FIG. 31(a).

FIG. 31(*a*) shows the light source mounted on a light source seat according to one embodiment of the present disclosure and FIG. 31(*b*) shows a top perspective view of FIG. 31(*a*).

Figure 32:
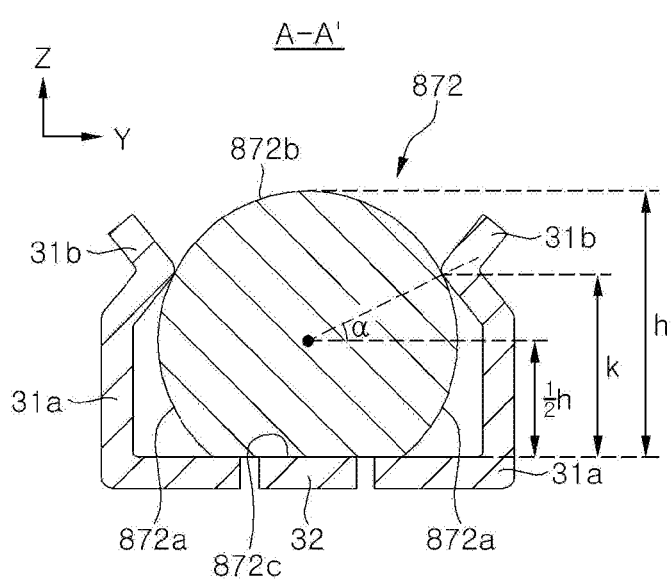
FIG. 32 is a cross-sectional view taken along line A-A' of FIG. 31.

FIG. 32 is a cross-sectional view taken along line A-A' of FIG. 31(*v*). FIG. 32 is a cross-sectional view taken along line A-A' of FIG. 31(*v*). Referring to FIG. 31, the light source seat 30 according to the present disclosure allows the light source 870, for example, the end caps 871, 872, to be seated thereon and includes a pressing member 31 and a securing member 32 having a unique structure by which the end caps 871, 872 can be pressed in a height direction and a thickness direction of the light source 870 to be stably secured and can be mounted on or separated from the light source seat without use of excessive force.

Referring to FIGS. 31(*a*) and (*b*), the light source seat 30 includes a support plate 33, the securing member 32, and the pressing member 31. As used herein, the longitudinal direction, thickness direction, and height direction of the light source 870 refer to the x-axis direction, y-axis, and z-axis direction in FIG. 31(*b*), respectively.

The support plate 33 may be provided in any suitable form to support the securing member 32 and the pressing member 31. For example, the support plate may be formed flat to efficiently distribute stress applied to a tongue portion 32a and a flat portion 32b from the end caps 871, 872, thereby improving durability.

The securing member 32 presses the light source 870 in the height direction of the light source 870 and includes the tongue portion 32a and the flat portion 32b, wherein the tongue portion 32a and the flat portion 32b may constitute, for example, a resilient piece. Herein, the term 'pressing' includes actions of contacting and pushing a target object. The tongue portion 32a and the flat portion 32b impart direct resilient force to the end cap 872. Here, the tongue portion 32a may adjoin the end cap 872 and the flat portion 32b may extend from the tongue portion 32a to be connected to the support plate 33. The tongue portion 32a has a substantially V or Λ-shaped oblique surface and the end cap 872 may contact the oblique surface of the tongue portion 32a. Here, the oblique surface of the tongue portion 32a may directly apply a force pressing the end cap 872 in the height direction of the light source 870, for example, in an upward direction from a lower surface of the light source 870. The flat portion 32b extends from the tongue portion 32a to be connected to the support plate 33 and may be flat to stably distribute resilient force applied to the tongue portion 32a to the support plate 33 while improving durability.

The pressing member 31 presses the light source 870, for example, the end cap 872, in the thickness direction of the light source 870 and may be configured to press the light source 870 in the y-axis direction from both sides of the end cap 872. The pressing member 31 includes a pressing member flat portion 31a extending from the support plate 33 in the height direction of the light source 870 and a pressing member bent portion 31a bent from the pressing member flat portion 31a toward the light source 870. Both the pressing member bent portion 31b and the pressing member flat portion 31a may be disposed on both sides of the end cap 872 and may constitute, for example, a resilient piece. The pressing member bent portion 31b is bent substantially in the form of '<' or '>' to contact a curved surface 872b of the end cap 872 to directly apply a force of pressing the end cap 872 in a substantially lateral direction of the end cap 872. The pressing member flat portion 31a may be formed flat to stably distribute resilient force applied to the pressing member bent portion 31b to the support plate 33 while improving durability.

Upon separation of the light source 870 from the light source seat 30, both restoration force of the pressing member bent portion 31b and restoration force of the pressing member flat portion 31a extending from the pressing member bent portion 31b act on the light source, and, when mounting the light source 870 on the light source seat 30, the restoration force of the pressing member flat portion 31a acts on the light source. Accordingly, upon separation of the light source 870 from the light source seat 30, larger restoration force acts on the light source than when mounting the light source 870 on the light source seat 30. According to the present disclosure, since the pressing member bent portion 31b is bent from the pressing member flat portion 31a, a user can separate the light source 870 from the light source seat 30 without use of excessive force, while the light source 870 mounted on the light source seat 30 can be prevented from being easily separated from the light source seat 30, thereby allowing stable installation of the light source.

Referring to FIG. 32, in the light source seat 30 according to the present disclosure, the securing member 32 presses the planar surface of the end cap 872 in the height direction of the light source 870 and the pressing member 31 presses the curved surfaces 872a, 872b of the end cap 872 in the thickness direction of the light source 870. The location of contact between the pressing member bent portion 31b and the curved surfaces 872a, 872b of the end cap 872 is higher than or equal to a preset height to allow the light source 870 to be stably secured while allowing installation and detachment of the light source 870 without use of excessive force, thereby improving durability of the light source seat 30 and improving efficiency in trapping insects such as flies.

Referring to FIGS. 31(a) and (b) and FIG. 32, the end cap 872 has the planar surface 872c and the curved surfaces 872a, 872b, wherein the planar surface 872c of the end cap 872 may be pressed by the tongue portion 32a of the securing member 32 in the height direction of the light source 870 and the curved surfaces 872a, 872b of the end cap 872 may be pressed by the pressing member bent portion 31b in the thickness direction of the light source 870. Here, the pressing member bent portion 31b may adjoin the curved surfaces 872a, 872b of the end cap 872 at a location k higher than half (½) h the height h of the end cap 872 such that the pressing member 31 and the securing member 32 apply pressing force to the end cap 872 in a substantially Y-shaped direction. That is, an angle α formed between a point at which the pressing member bent portion 31b contacts the end cap 872 and the planar surface of the end cap 872 may be greater than 0° and less than 50°, for example, 30° to 45°. If the angle α is less than 0°, the pressing member 31 cannot sufficiently support the end cap 872 in a downward direction against upward pressing force of the securing member 32 with respect to the end cap 872, causing the end cap 872 to be easily separated from the light source seat 30. In addition, if the angle α is greater than 50°, excessive force can be required to seat the end cap 872 on the light source seat 30. Specifically, in the process of seating the end cap 872 on the light source seat 30, contact between the curved surfaces 872a, 872b and the bent portion 31b occurs over a length corresponding to 2a (that is, length of arc=central angle (rad)×radius) or over an area corresponding thereto. With increasing a, the contact length or area and frictional force between the curved surfaces and the bent portion in the process of seating the end cap 872 on the light source seat 30 also increase. Accordingly, if the angle α is greater than 50°, excessive force is required to seat the end cap 872 on the light source seat 30, causing deterioration in durability of each component of the adhesive-type insect trap or causing decay of collected insects at the bottom of the insect trap and thus significant deterioration in trapping efficiency.

Referring again to FIG. 28 and FIG. 29, the adhesive-type insect trap includes at least one light source support member 10, 20 which supports the light source 870 mounted on the light source mount 430. The light source support member 10, 20 supports the light source 870 such that the light source 870 is separated a predetermined distance from the main body 410, thereby preventing deformation of an adhesive material of the adhesive sheet 140, 240, 340, 440, 540 or 640 or warpage of the adhesive sheet 140, 240, 340, 440, 540 or 640 due to heat from the light source 870 which would otherwise be located excessively close to the adhesive sheet 140, 240, 340, 440, 540 or 640. In addition, the light source support member 10, 20 may be formed of a material capable of easily dissipating heat from the light source 870 so as to further prevent deformation of the adhesive sheet 140, 240, 340, 440, 540 or 640.

Although the light source support member 10, 20 is not limited to a particular shape, the light source support member may include a flat plate corresponding to the planar surface 872c of the end cap 871 or 872 of the light source 870, wherein the flat plate of the light source support member 10, 20 may be separated a predetermined distance from the main body bottom 410a such that the planar surface 872c of the end cap 871 or 872 can be seated on the flat plate. For example, the light source support member 10, 20 may include plural light source support members disposed on the main body bottom 410a and separated predetermined distances from the side portions 411a, 411b disposed at respective opposite sides of the main body 410. For example, a first light source support member 10 may be disposed on both sides of the stopper unit 413 to allow securing of the adhesive sheet 140, 240, 340, 440, 540 or 640 by the stopper unit 413 and efficient utilization of the internal space of the main body 40, thereby improving efficiency in trapping flies and the like. For example, a second light source support member 20 may be separated a predetermined distance from the side portion 411b, in which the light source seat 30 is disposed, and may be provided in the form of a single plate to efficiently discharge heat from the light source 870 to the outside to generate decoy heat attracting insects such as flies, thereby improving insect trapping efficiency.

The light source support members 10, 20 may include at least one light source-pressing member 11 or 21 pressing the light source 870 in the thickness direction of the light source 870. The light source-pressing member 11 or 21 may have the same configuration and effects as the pressing member 31 described above, and may press and secure at least a portion of the case of the light source 870. For example, the light source-pressing member 11 or 21 may include a light source-pressing member flat portion (not shown) and a light source-pressing member bent portion (not shown) which correspond to the pressing member flat portion 31a and the pressing member bent portion 31b, respectively. That is, the case of the light source 870 may include the same features as the end cap 871 or 872 at least a portion thereof, for example, at a portion thereof contacting the light source-pressing member 11 or 21, such that the light source-pressing member 11 or 21 can press the case in the same way that the pressing member 31 presses the end cap 872.

The light source support members 10, 20 can easily dissipate heat generated from the light source 870. For example, a portion of the light source support members 10, 20 adjoining the light source 870 may include a metal having high thermal conductivity, for example, at least one selected from among Ag, Cu, Au, Al, and Mo.

Accordingly, with the light source support members 10, 20 formed of a material having high heat dissipation efficiency and supporting the light source 870 such that the light source 870 is separated a predetermined distance from the adhesive sheet 140, 240, 340, 440, 540 or 640, the adhesive-type insect trap according to the present disclosure can prevent deformation of the adhesive sheet 140, 240, 340, 440, 540 or 640, thereby improving efficiency in trapping insects such as flies. In addition, with the light source-pressing member 11 or 21 provided to the light source support members 10, 20, the adhesive-type insect trap according to the present disclosure can allow both stable securing of the light source 870 and installation and detachment of the light source 870 without use of excessive force, thereby improving durability of each component of the insect trap while improving efficiency in trapping insects such as flies.

Figure 34:
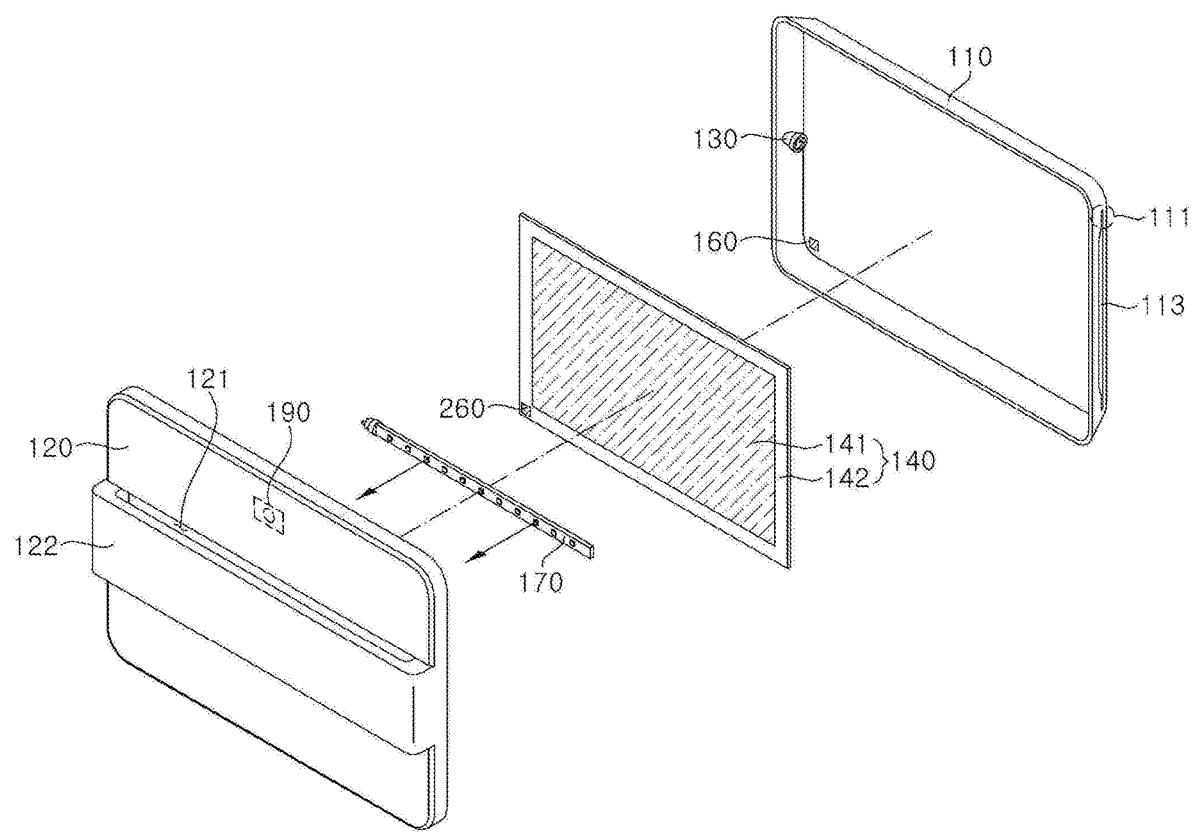
FIG. 34 shows an adhesive-type insect trap according to one embodiment of the present disclosure.

FIG. 34 shows an adhesive-type insect trap according to one embodiment of the present disclosure. Referring to FIG. 34, the adhesive-type insect trap 1000, 2000, 3000, 4000, 5000, 6000, 7000, 8000, 9000, 1100 or 1200 may include a camera 190 to allow a user to observe insects trapped on the adhesive sheet 140, 240, 340 or 440. The camera 190 may have a zoom function, whereby a user can move the camera 190 or use the zoom function at a remote location through transmission of a signal to a communication module mounted on the adhesive-type insect trap 1000, 2000, 3000, 4000, 5000, 6000, 7000, 8000, 9000, 1100 or 1200 when photographing insects trapped in the adhesive-type insect trap 1000, 2000, 3000, 4000, 5000, 6000, 7000, 8000, 9000, 1100 or 1200. For example, the camera 190 may include a fisheye lens. The fisheye lens is an ultra-wide angle lens having an angle of view of greater than 180 degrees and may include a lens providing a wide viewing range of 180 degrees. With the fisheye lens, the camera 190 can observe the entire adhesive sheet 140, 240, 340, 440, 540 or 640 without a separate rotation function or zoom function to identify the types of trapped insects or to ascertain an area of the adhesive sheet 140, 240, 340, 440, 540 or 640 in which insects are trapped. That is, with the fisheye lens, the camera 190 can photograph or observe the entirety of the adhesive sheet 140, 240, 340, 440, 540 or 640 even in a compact interior of the adhesive-type insect trap, thereby allowing efficient utilization of the internal space of the adhesive-type insect trap. Further, with the camera, a user can identify the types of trapped insects to ascertain whether insects known to transmit viruses are trapped and can determine in advance when to replace the adhesive sheet 140, 240, 340, 440, 540 or 640, thereby preventing deterioration in efficiency of trapping insects.

In addition, the adhesive-type insect trap 1000, 2000, 3000, 4000, 5000, 6000, 7000, 8000, 9000, 1100 or 1200 may include a sensor to allow a user to ascertain the presence of insects trapped in the insect trap or to ascertain an area of the adhesive sheet 140, 240, 340 or 440 occupied by insects trapped thereon, and may perform a notification function to a user through the communication module when the sensor detects that insects are trapped or that the area of the adhesive sheet occupied by insects trapped thereon exceeds a preset value. By way of example, the sensor may include a brightness sensor for detecting brightness of the adhesive sheet 140, 240, 340 or 440. The brightness sensor may detect the amount of trapped insects through a difference in brightness between a region of the adhesive sheet to which insects are attached and a region of the adhesive sheet to which no insects are attached.

Further, the adhesive-type insect trap 1000, 2000, 3000, 4000, 5000, 6000, 7000, 8000, 9000, 1100, 1200 may include an insect attractant spray (not shown) or may include an insect attractant contained in the adhesive sheet to improve insect attraction efficiency.

Further, the adhesive-type insect trap 1000, 2000, 3000, 4000, 5000, 6000, 7000, 8000, 9000, 1100 or 1200 may include a light diffusion material deposited or coated onto the adhesive sheet 140, 240, 340 or 440 to diffuse light emitted from the light source 170, 270, 370, 470, 570, 670 or 770, thereby improving efficiency in attraction of insects, particularly flies.

Insects, particularly flies, tend to be more strongly attracted to refracted or diffused light than to direct light. The adhesive-type insect trap 1000, 2000, 3000, 4000, 5000, 6000, 7000, 8000, 9000, 1100 or 1200 can refract or diffuse light emitted from the light source 170, 270, 370, 470, 570, 670 or 770, thereby improving efficiency in attraction of insects with decoy light. By way of example, the cover 120, 220 or 320 may have a roughened surface, may include a separate diffusion film attached thereto or coated thereon, or may include a diffusion agent applied thereto or coated thereon, wherein the surface of the cover 120, 220 or 320 includes outer and inner surfaces of the cover 120, 220 or 320. By way of another example, the reflector 150 or 250 may be a roughened surface, may include a separate diffusion film attached thereto or coated thereon, or may include a diffusion agent applied thereto or coated thereon. By way of a further example, the light source 170, 270, 370, 470, 570, 670 or 770 may have a roughened surface, may include a separate diffusion film attached thereto or coated thereon, or may include a diffusion agent applied thereto or coated thereon. For example, the case 174 of the light source 770 as shown in FIG. 17 may have a roughened surface, may include a separate diffusion film attached thereto or coated thereon, or may include a diffusion agent applied thereto or coated thereon.

Figure 35:
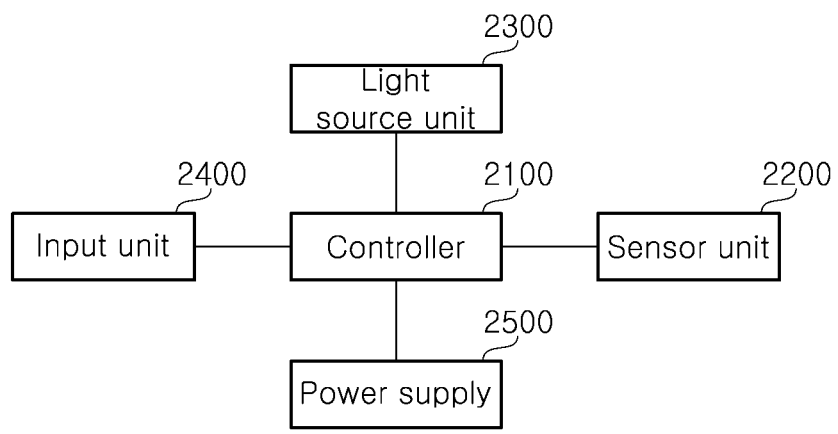
FIG. 35 is a block diagram of the adhesive-type insect trap according to the embodiments of the present disclosure.
Figure 36:
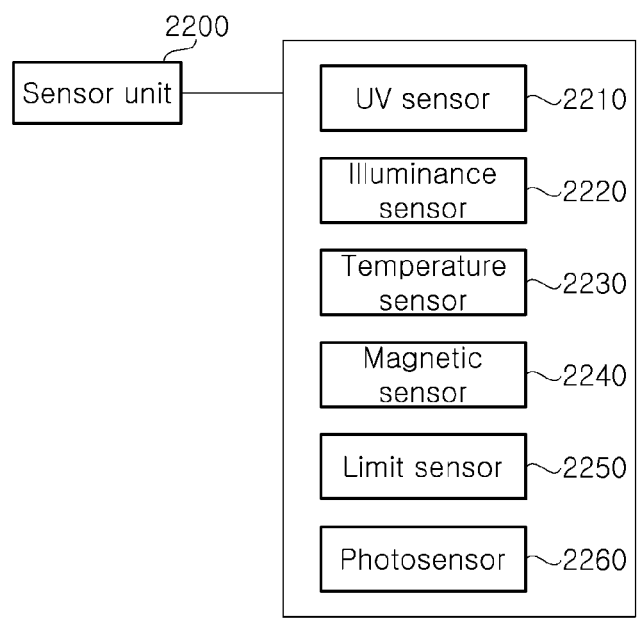
FIG. 36 is a block diagram of a sensor unit according to embodiments of the present disclosure.

FIG. 35 is a block diagram of the adhesive-type insect trap according to the embodiments of the present disclosure. Referring to FIG. 35, the adhesive-type insect trap 1000, 2000, 3000, 4000, 5000, 6000, 7000, 8000, 9000, 1100 or 1200 may include a controller 2100, a sensor unit 2200, a light source unit 2300, an input unit 2400, and a power supply 2500. The controller 2100 may control operation of the adhesive-type insect trap, for example, operation of the light source unit 2300, based on input information. The controller 2100 may process at least part of information obtained from the sensor unit 2200 to provide the processed information to a user in various ways or to control operation of the light source unit 2300 based on the processed information.

The power supply 2500 supplies electric power to the adhesive-type insect trap and may be charged using a general AC power source or may include a battery. The power supply 2500 may include a filter, a rectifier, a switching converter, and an output unit. The filter prevents internal components of the power supply 2500 from being damaged by noise on an input line and removes high-frequency noise over the audio band, thereby allowing stable current supply. The rectifier may be composed of a rectifying circuit, a smoothing circuit, and a constant voltage circuit. The rectifying circuit filters only the positive polarity from an alternating current that oscillates at 50 Hz to 60 Hz per second, the smoothing circuit converts a pulsed current into a constant voltage using a rectifier capacitor keeping a voltage constant, and the constant voltage circuit may be composed of a constant voltage diode producing a stable and constant direct current and a transistor. The switching converter may reduce electric power converted into a constant current by the rectifier into DC power required by a phototherapy apparatus. The output unit may supply power to the light source unit 2300.

The light source unit 2300 may be operated in response to an operation signal from the controller 2100. For example, based on information detected by the sensor unit 2200, the controller 2100 may control power supply to the light source unit 2300 or control driving of the light source 170, 270, 370, 470, 570, 670 or 770.

By way of example, the controller 2100 may control operation of the light source through control over the current, voltage, pulse-width modulation, or phase-cut of the light source depending upon whether illuminance of ambient light detected by an illuminance sensor 2220 falls within a preset illuminance range. For example, when the illuminance of ambient light detected by the illuminance sensor 2220 exceeds the preset illuminance range, the controller 2100 may increase light output by setting the duty ratio of a PWM signal to 70%, and, when the illuminance of ambient light detected by the illuminance sensor 2220 is less than the preset illuminance range, the controller 2100 may reduce light output by setting the duty ratio of a PWM signal to 50%, thereby providing efficient power consumption while preventing a user from suffering inconvenience such as dazzling. Here, the term "duty ratio" refers to a ratio of pulse-on duration to the total duration of one cycle, and a higher duty ratio indicates a higher light output for a given period of time.

By way of example, when the temperature around the light source 170, 270, 370, 470, 570, 670 or 770 detected by a temperature sensor 2230 exceeds a preset temperature range, the controller 2100 may send a signal for cutting off power supply to the light source 170, 270, 370, 470, 570, 670 or 770 to the light source unit 2300 to prevent short circuit of the light source 170, 270, 370, 470, 570, 670 or 770, thereby improving the durability and safety in use of the adhesive-type insect trap 2000.

By way of example, the controller 2100 may control operation of the light source 170, 270, 370, 470, 570, 670 or 770 based on information detected by a magnetic sensor 2240 or limit sensor 2250 that detects whether the adhesive sheet 140, 240, 340, 440, 540 or 640 is inserted and whether the cover 120, 220 or 320 is detached. For example, when the adhesive sheet 140, 240, 340, 440, 540 or 640 is incompletely inserted or the cover 120, 220 or 320 is incompletely attached to the main body 110, 210 or 310, the controller 2100 may send a signal for cutting off power supply to the light source 170, 270, 370, 470, 570, 670 or 770 to the light source unit 2300 after receiving corresponding information detected by the magnetic sensor 2240 or the limit sensor 2250. That is, when the adhesive sheet 140, 240, 340, 440, 540 or 640 is incompletely inserted or the cover 120, 220 or 320 is incompletely attached, the adhesive-type insect trap shuts off operation of the light source 170, 270, 370, 470, 570, 670 or 770 to inform a user of incomplete insertion of the adhesive sheet or incomplete attachment of the cover, thereby improving insect trapping efficiency.

The input unit 2400 may be provided in the form of a keyboard including various keys such as character buttons, symbol buttons, special buttons and the like to receive user's input or may be provided in the form of a simple switch. Although not shown in the drawings, for the adhesive-type insect trap 2000 further including a display unit (not shown), the display unit may be implemented by, for example, a touchscreen panel. Here, the keyboard included in the input unit 2400 may be displayed to overlap a touchscreen in graphical form. Here, the location and transparency of a keyboard input window is adjustable by a user and the touchscreen panel may include an input means that serves as a display means and registers input by detecting the touch of a finger or stylus on a surface thereof.

Although not shown in the drawings, the adhesive-type insect trap may further include the display unit (not shown). The display unit may display a window, for example, a graphical user interface (GUI), displaying information on operation of each component of the adhesive-type insect trap, operation of which is controlled by the controller 2100, for example, information on operation of the light source 170, 270, 370, 470, 570, 670 or 770 or information detected by the sensor unit 2200, and may be disposed, for example, on a front surface of the cover 120, 220 or 320. The display unit may be implemented by a display window such as an LCD or an LED, or may be implemented by a touchscreen panel serving as both an input means and a display means.

Although not shown in the drawings, the adhesive-type insect trap may further include an alarm generator (not shown). When a data value detected by the sensor unit 2200 exceeds or is less than a preset data value, the controller 2100 may send an alarm generation signal to the alarm generator. Here, an alarm generated by the alarm generator may be a sound alarm or a light alarm and may be issued from an electronic device of a user, for example, a portable terminal, through a communication module. By way of example, when the luminous intensity of the light source 170, 270, 370, 470, 570, 670 or 770 detected by a UV sensor 2210 is less than a preset luminous intensity range, the alarm generator may generate an alarm, wherein the alarm may serve as a light source replacement signal. By way of another example, when the temperature around the light source 170, 270, 370, 470, 570, 670 or 770 detected by the temperature sensor 2230 exceeds a preset temperature range, the alarm generator may generate an alarm, wherein the alarm may serve as a signal warning that the light source 170, 270, 370, 470, 570, 670 or 770 is in danger. By way of a further example, when the magnetic sensor 2240 or the limit sensor 2250 detects that the adhesive sheet 140, 240, 340, 440, 540 or 640 is not inserted or that the cover 120, 220, 320 is incompletely attached, the alarm generator may generate an alarm, which may serve as a not-ready signal.

The sensor unit 2200 may include various sensors, specifically, the UV sensor 2210, the illuminance sensor 2220, and the temperature sensor 2230, the magnetic sensor 2240, the limit sensor 2250, and an optical sensor 2260, as shown in FIG. 20. Functions of each sensor are the same as described above.

Figure 37:
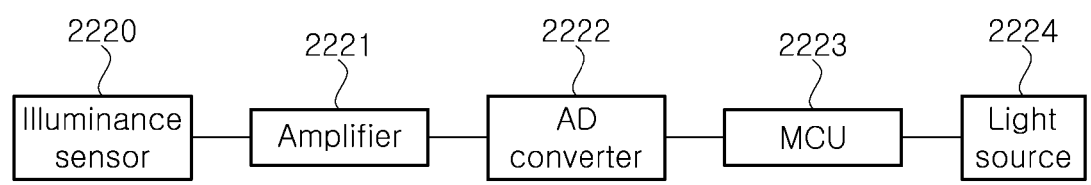
FIG. 37 is a block diagram illustrating light source control by an illuminance sensor according to the present disclosure.

FIG. 37 is a block diagram illustrating light source control by an illuminance sensor according to the present disclosure. The adhesive-type insect trap can detect the illuminance of ambient light using the illuminance sensor 2220 to control operation of the light source 170, 270, 370, 470, 570, 670 or 770 based on the detected illuminance. Referring to FIG. 37, the adhesive-type insect trap may include the illuminance sensor 2220, an amplifier 2221, an analog-digital converter (ADC) 2222, a microcontroller unit (MCU) 2223, and a light source 2224. Here, the light source 2224 may refer to at least one of the light source 170, 270, 370, 470, 570, 670 or 770 described above.

By way of example, once the illuminance of ambient light is detected by the illuminance sensor 2220 (ambient light sensor), before signal processing by the ADC, the amplifier (Amp) 2221 may perform signal processing such that an analog signal can remain close to an original form thereof without being altered by noise or the like or can be under appropriate conditions for processing by the ADC. Here, analog signal processing by the amplifier 2221 may be mainly composed of amplification and filtering for noise cancellation. Further, for analog signal processing, an analog signal chain including the amplifier 2221 may be employed.

For example, the MCU 2223 may include a CPU core, a memory, and a programmable input/output, wherein a program for the MCU may be compiled and downloaded to the MCU as machine code. Specifically, the MCU 2223 may control operation of the light source 2224 based on ambient illuminance detected by the illuminance sensor 2220. In addition, the MCU 2223 may be replaced by the controller 2100 describe above or may be included in the controller 2100 as a subcomponent. For example, the MCU 2223 may control operation of the light source 2224 through control over the current, voltage, pulse-width modulation (PWM), or phase-cut of the light source 2224. For example, when the ambient illuminance detected by the illuminance sensor 2220 exceeds a preset ambient illuminance range, the MCU 2223 may control operation of the light source 2224, for example, light output of the light source, by generating an operation signal for increasing the driving current, drive voltage, or PWM duty ratio of the light source 2224.

Figure 38:
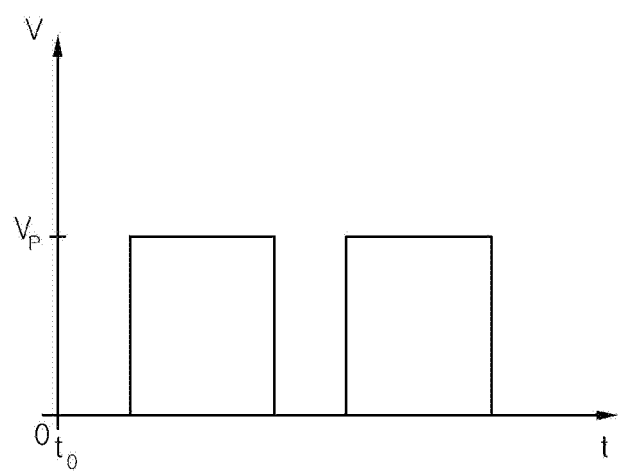
FIG. 38, FIG. 39 and FIG. 40 are graphs showing waveforms of drive voltages having different duty ratios depending on PWM control for a light source according to the present disclosure.
Figure 39:
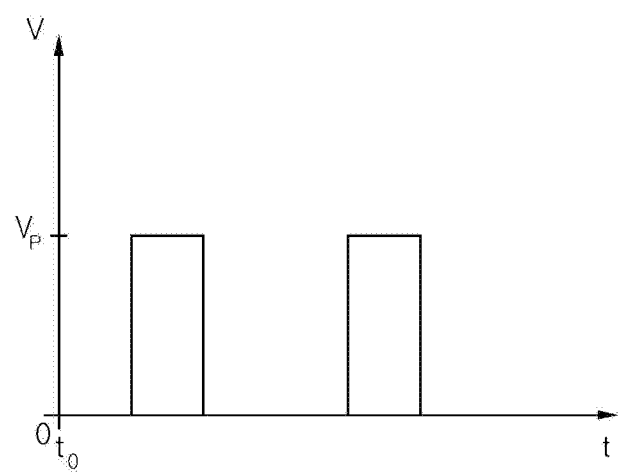
Figure 40:
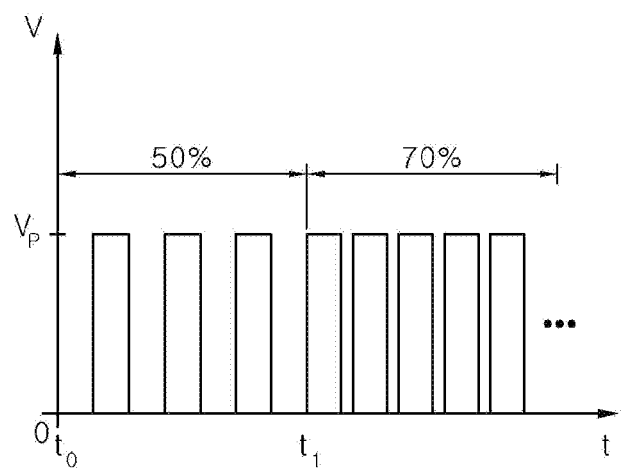

By way of example, the MCU 2223 may control operation of the light source 2224 by PWM control. FIG. 38, FIG. 39 and FIG. 40 are graphs showing waveforms of drive voltage having different duty ratios depending on PWM control for the light source 2224 according to the present disclosure. Referring to FIG. 38 to FIG. 40, the drive voltage Vp applied to the light source 2224 may be controlled through PWM according to a PWM signal generated by the MCU 2223. PWM control is a control method in which a light source is operated by pulsed current rather than direct current, and can allow reduction in driving current for a given light output and allow a larger amount of current to flow than a continuous driving method, thereby increasing light radiation range. That is, through PWM control over the light source 2224, the adhesive-type insect trap can improve efficiency in attraction of insects with decoy light, thereby improving pest trapping efficiency while allowing efficient power consumption.

For example, in the daytime or in an environment of high ambient illuminance, a user may input a signal for increasing light output of the light source 2224 through the input unit 2400. Here, the controller 2100 may send a signal for increasing the duty ratio for PWM driving to the light source 2224, whereby PWM control at a high duty ratio as shown in FIG. 38 can be achieved to increase light output of the light source 2224, thereby improving efficiency in attraction of insects with decoy light and thus improving pest trapping efficiency.

For example, at night or in an environment of low ambient illuminance, a user may input a signal for reducing light output of the light source 2224 through the input unit 2400. Here, the controller 2100 may send a signal for reducing the duty ratio for PWM driving to the light source 2224, whereby PWM control at a low duty ratio as shown in FIG. 39 can be achieved to reduce light output of the light source 2224, thereby preventing unnecessary power waste and dazzling and thus improving user friendliness without deterioration in efficiency in attraction of insects with decoy light and thus pest trapping efficiency.

For example, when ambient illuminance changes, the light output of the light source 2224 may be automatically controlled according to the ambient illuminance detected by the illuminance sensor 2220 without a separate signal which is input by a user through the input unit 2400 to control the light output of the light source 2224. For example, referring to FIG. 40, when the ambient illuminance is low, the MCU 2223 may send a PWM signal having a relatively low duty ratio, for example, a duty ratio of 50%, to the light source 2224, and, when the ambient illuminance gradually increases and falls within a preset ambient illuminance range, the MCU 2223 may send a PWM signal having a relatively high duty ratio, for example, a duty ratio of 70%, to the light source 2224. That is, through control over the duty ratio of a PWM signal, the adhesive-type insect trap 2000 allows the light output of the light source 2224 to be automatically controlled according to the ambient illuminance without directly changing voltage or current and thus can improve efficiency in attraction of insects with decoy light, thereby improving insect pest trapping efficiency while preventing unnecessary power waste and dazzling and thus improving user friendliness.

Here, the preset ambient illuminance range may include several sections. For example, when a value of ambient illuminance corresponds to section A, section B, section C, . . . , or section n, the MCU 2223 may send a PWM signal having a duty ratio of A'%, B'%, C'%, ..., or n'% to the light source. That is, the adhesive-type insect trap can perform control such that light output of the light source can be changed stepwise according to change in ambient illuminance, and thus can improve efficiency in attraction of insects with decoy light, thereby improving insect pest trapping efficiency while preventing unnecessary power waste and dazzling and thus improving user friendliness.

Figure 41:
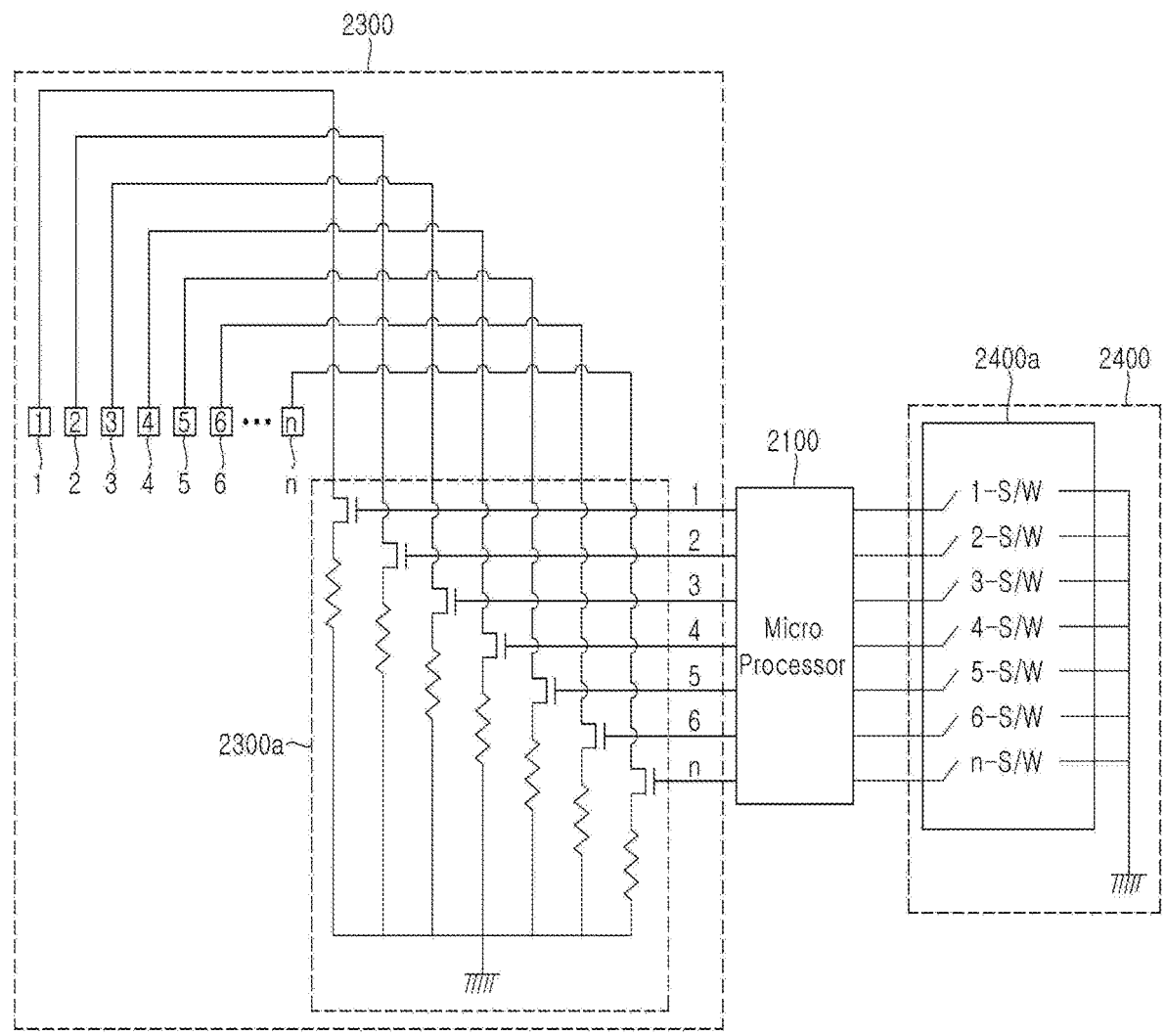
FIG. 41 is a schematic circuit diagram of a light source according to one embodiment of the present disclosure.

FIG. 41 is a schematic circuit diagram of a light source according to one embodiment of the present disclosure. Referring to FIG. 41, the light source 170, 270, 370, 470, 570, 670 or 770 may include a plurality of LEDs 1, 2, 3, 4, 5, 6, ..., n, wherein each of the LEDs 1, 2, 3, 4, 5, 6, ..., n may be individually operated. Specifically, the plurality of LEDs may be sequentially or alternately operated according to a control signal generated by the controller 2100. For example, when the ambient illuminance detected by the illuminance sensor 2220 is less than the preset ambient illuminance range, only a first LED 1, a third LED 3, a fifth LED 5, ..., and an nth LED n may be powered, and, when the ambient illuminance detected by the illuminance sensor 2220 exceeds the preset ambient illuminance range, all of the LEDs 1, 2, 3, 4, 5, 6, ..., n may be powered. In addition, when the preset ambient illuminance range includes several sections, the light source may be operated such that the number of powered LEDs 1, 2, 3, 4, 5, 6, ..., n can be increased stepwise.

Here, an LED input switch 2400a is a switch for selecting at least one of the first LED 1, the second LED 2, the third LED 3, the fourth LED 4, the fifth LED 5, the sixth LED 6, ..., and the nth LED n, and may be divided into 1-S/W, 2-S/W, 3-S/W, 4-S/W, 5-S/W, 6-S/W, ..., n-S/W, wherein the input unit 2400 may be provided with a button to send electric signals to the switches in a collective or individual manner. In addition, the first to $n^{th}$ LEDs 1, 2, 3, 4, 5, 6, ..., n may be interconnected in groups of the same type to be connected to a light source driving circuit 2300a, wherein the light source driving circuit 2300a may be connected to the controller 2100 to be switched on/off.

In addition, the adhesive-type insect trap may include a UV sensor 2210 detecting intensity of light emitted from the light source 170, 270, 370, 470, 570, 670 or 770 and may emit an alarm sound to alert a user before end of life of the light source 170, 270, 370, 470, 570, 670 or 770. For example, the adhesive-type insect trap may display a light source replacement signal through the alarm generator described above. For example, when the intensity of light emitted from the LED 1, 2, 3, 4, 5, 6, ..., or n measured by the UV sensor 2210 is less than a preset value, the adhesive-type insect trap may generate the light source replacement signal. Typical UV sensors estimate future life of a light source based on accumulated amount of light emitted from the light source. Accordingly, when a plurality of LEDs, for example, filament-type LEDs or tube-type LEDs, is mounted on the light source, such typical UV sensors cannot accurately determine which LED has reached end of life, causing unnecessary waste due to replacement of the light source or causing belated replacement of the light source and thus deterioration in efficiency in attraction of insects with decoy light and insect trapping efficiency.

Conversely, the adhesive-type insect trap according to the present disclosure enables individual driving of each of the LEDs 1, 2, 3, 4, 5, 6, ..., n, and can detect the intensity of light from each of the LEDs 1, 2, 3, 4, 5, 6, ..., n using the UV sensor 2210, thereby allowing determination of when to replace each individual LED 1, 2, 3, 4, 5, 6, ..., or n, rather than when to replace the entire light source 170, 270, 370, 470, 570, 670 or 770. For example, when a user presses a "display light source time for replacement" button displayed on the input unit 2400 or touches a touch panel, the number of an LED 1, 2, 3, 4, 5, 6, ..., or n having a luminous intensity of less than the preset value may be displayed on the display unit as the UV sensor 2210 is operated while the LEDs 1, 2, 3, 4, 5, 6, ..., n mounted on the light source 170, 270, 370, 470, 570, 670 or 770 are sequentially operated. That is, with the UV sensor detecting luminous intensity of each of LEDs 1, 2, 3, 4, 5, 6, ..., n, the adhesive-type insect trap can prevent waste due to replacement of the light source 170, 270, 370, 470, 570, 670 or 770 itself and deterioration in efficiency of attracting insects with decoy light, thereby improving insect trapping efficiency.

In addition to detecting the intensity of light emitted from the light source 170, 270, 370, 470, 570, 670 or 770 to inform a user of a time for replacement of the light source 170, 270, 370, 470, 570, 670 or 770, the UV sensor 2210 can check driving errors, such as whether a light source 170, 270, 370, 470, 570, 670 or 770 or LED 1, 2, 3, 4, 5, 6, ..., or n other than a light source 170, 270, 370, 470, 570, 670 or 770 or LED 1, 2, 3, 4, 5, 6, ..., or n selected by a user through the input unit 2400 is operated, or whether a light source 170, 270, 370, 470, 570, 670 or 770 or LED 1, 2, 3, 4, 5, 6, ..., or n selected by a user is operated at a preset light output value, thereby preventing power loss due to driving errors, which can be caused by use of the plurality of light sources 170, 270, 370, 470, 570, 670, 770 or the plurality of LEDs 1, 2, 3, 4, 5, 6, ..., n.

Figure 42:
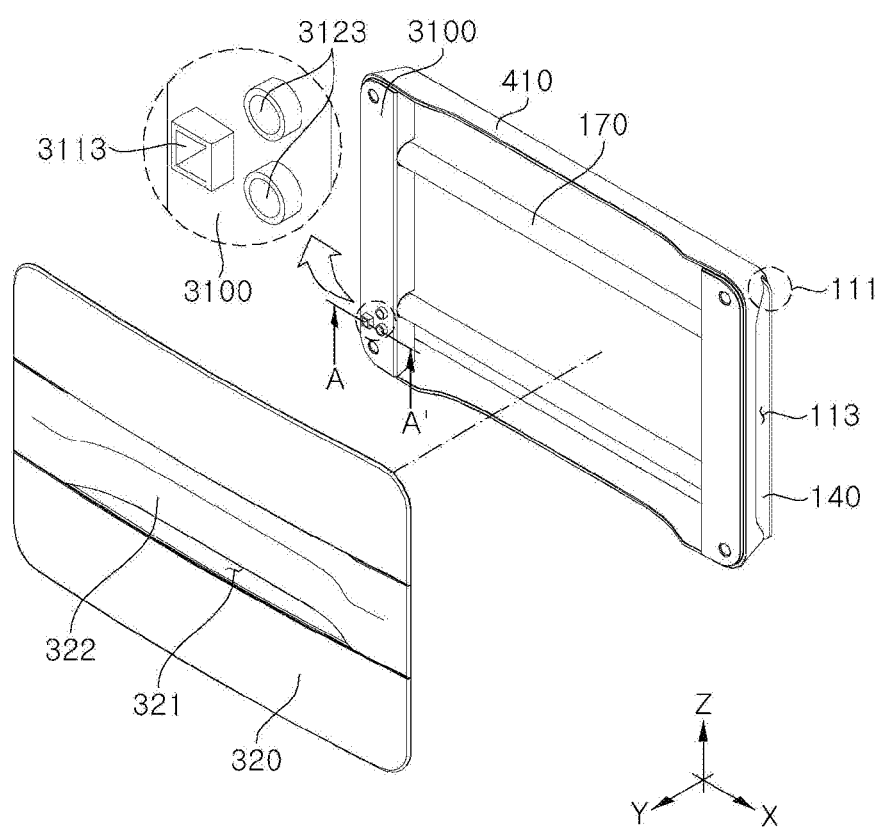
FIG. 42 is a partially enlarged view of a side portion of the adhesive-type insect trap according to embodiments of the present disclosure.
Figure 43:
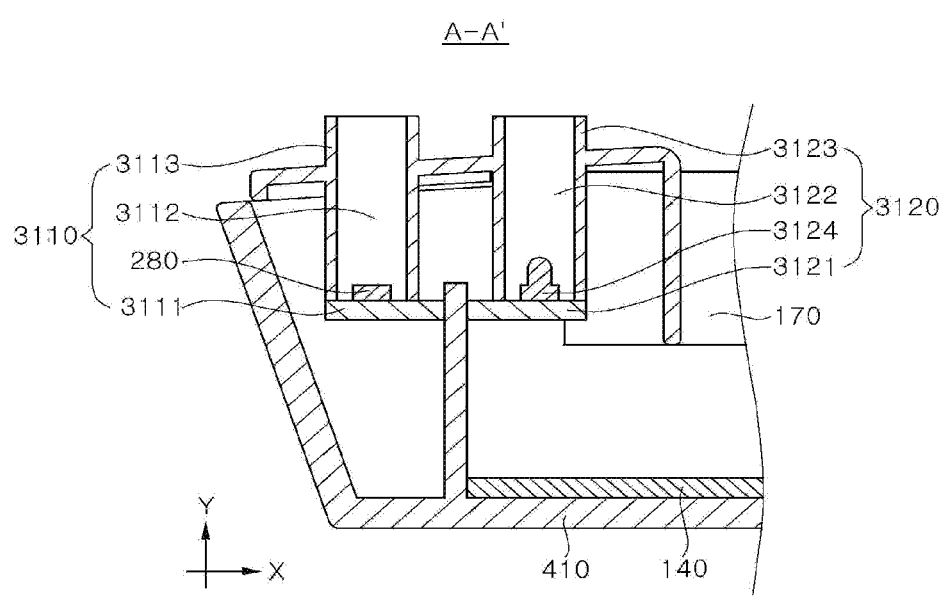
FIG. 43 is a cross-sectional view taken along line A-A' of FIG. 42.

FIG. 42 is a partial enlarged view of a side portion of the adhesive-type insect trap according to embodiments of the present disclosure and FIG. 43 is a cross-sectional view taken along line A-A' of FIG. 42. An adhesive-type insect trap 1300 shown in FIG. 42 and FIG. 43 may have the same configuration as the adhesive-type insect trap 1000, 2000, 3000, 4000, 5000, 6000, 7000, 8000, 9000, 1100 or 1200 described above, for example, the adhesive-type insect trap 1100 or 1200 described with reference to FIG. 20 to FIG. 23, except for the configuration of a side portion 3100.

Referring to FIG. 42, the adhesive-type insect trap 1300 may further include a side portion 3100 disposed in a side region of the main body 410. The side portion 3100 may adjoin the side surfaces of the main body 410 or may be separated a predetermined distance from the main body 410. For example, the side portion 3100 may be disposed to adjoin the side surfaces of the main body 410 to allow efficient use of a space defined in the main body 410. The side portion 3100 may be provided with circuits (not shown) and a power supply (not shown), which supplies power to the light source 170, 270, 370, 470, 570, 670 or 770, a sensor 280, an indication light source 3124 and the like and may include a separate housing to prevent damage to the power supply and the circuit due to intrusion of insects or dust. Here, the light source mount 130 may be at least partially connected to the side portion 3100. For example, the light source mount 130 may be disposed outside the side portion 3100 or may be mounted within the side portion 3100.

Referring to FIG. 42 and FIG. 43, the side portion 3100 may be provided with a sensor installation unit 3110. The sensor installation unit 3110 may include a sensor seat 3111 and a sensor guide 3112. The sensor seat 3111 allows the sensor 280 to be stably installed thereon and may include a circuit supplying power to the sensor 280. The sensor 280 may include the sensor 180 described above, for example, a sensor detecting information about at least one of the types of insects trapped on the adhesive sheet 140, the area of the adhesive sheet 140 occupied by trapped insects, the contrast of the adhesive sheet 140, the temperature around the light source 170, the intensity of light emitted from the light source 170, the illuminance of ambient light of the adhesive-type insect trap 1300, whether the adhesive sheet 140 is inserted, and whether the cover 120 is detached. For example, the sensor 280 may include a UV sensor, an illuminance sensor, a temperature sensor, a magnetic sensor, a limit sensor, and an optical sensor.

The sensor guide 3112 may guide light emitted from the outside of the adhesive-type insect trap 1300 to reach the sensor seat 3111. The sensor guide 3112 may be a substantially straight hole extending to a space provided with the sensor seat 3111 along a groove formed on a surface of the side portion 3100 or may include a bent section when provided with a reflector (not shown). An illuminance sensor may be disposed on the sensor seat 3111. A typical illuminance sensor detects ambient light along with light emitted from an apparatus equipped with the illuminance sensor, such as, an adhesive-type insect trap, for example, decoy light or sensor light, and thus has difficulty in accurately determining the illuminance of the ambient light. In the adhesive-type insect trap according to the present disclosure, since the illuminance sensor is disposed at the sensor seat 3111, which is formed inside the side portion 3100 to be separated a predetermined distance from the surface of the side portion 3100, the illuminance sensor can sense light emitted from the outside of the adhesive-type insect trap 1300 while hardly sensing light emitted from separate light sources mounted on the adhesive-type insect trap 1300, thereby exhibiting improved detection efficiency and accuracy.

In addition, the sensor installation unit 3100 may further include a sensor installation unit protrusion 3113 protruding from the side portion 3100. The sensor installation unit protrusion 3113 protrudes a predetermined distance from the surface of the side portion 3100 to prevent the illuminance sensor from sensing light emitted from the separate light sources installed in the adhesive-type insect trap 1300, thereby improving illuminance detection efficiency. For example, a display unit 3120 may be disposed on the side portion 3100 to allow efficient utilization of the internal space of the main body 410 and may be disposed in proximity to the sensor installation unit 3110 to allow efficient circuit configuration. With the sensor installation unit protrusion 3113, the adhesive-type insect trap 1300 can prevent the illuminance sensor from being irradiated with indication light emitted from the display unit, thereby improving illuminance detection efficiency and accuracy.

The side portion 3100 may be further provided with the display unit 3120. As described above, the display unit 3120 may be implemented by, for example, a touchscreen panel, and the keyboard included in the input unit 2400 may be displayed to overlap a touchscreen in graphical form. Here, the location and transparency of a keyboard input window is adjustable by a user and the touchscreen panel may include an input means that serves as a display means and also registers input by detecting touch of a finger or stylus on a surface thereof. For example, the display unit 3120 may include a window displaying information on operation of the light source 170, 270, 370, 470, 570, 670 or 770 or information detected by the sensor unit 2200 and may be implemented by a display window such as an LCD or an LED or as a touchscreen panel serving as both an input means and a display means.

When a value of data detected by the sensor unit 2200 exceeds or is less than a preset data value, the controller 2100 may send an alarm generation signal to the display unit 3120, which, in turn, may emit indication light in response thereto. For example, when the luminous intensity of the light source 170, 270, 370, 470, 570, 670 or 770 is less than a preset luminous intensity range, the display unit 3120 may emit indication light, wherein the indication light may serve as a light source replacement signal. For example, when the temperature around the light source 170, 270, 370, 470, 570, 670 or 770 detected by the temperature sensor 2230 exceeds a preset temperature range, the display unit 3120 may emit indication light, wherein the indication light may serve as a signal warning that the light source 170, 270, 370, 470, 570, 670 or 770 is in danger. For example, when the magnetic sensor 2240 or the limit sensor 2250 detects that the adhesive sheet 140, 240, 340, 440, 540 or 640 is not inserted or that the cover 120, 220, 320 is incompletely attached, the display unit 3120 may emit indication light, wherein the indication light may serve as a not-ready signal.

The display unit 3120 may include an indication light source seat 3121, an indication light source guide 3122, and a display unit protrusion 3123. The indication light source seat 3121 allows the indication light source 3124 to be stably installed thereon, and may be provided with a circuit controlling power supply to the indication light source 3124 or operation of the indication light source 3124. The indication light source guide 3122 guides light emitted from the indication light source 3124 disposed on the indication light source seat 3121 to reach an outside of the side portion, thereby preventing the illuminance sensor from sensing the light from the indication light source 3124, and may be provided in the same form as the sensor guide 3112 described above. The display unit protrusion 3123 protrudes from the side portion 3100 and may be provided in the same form as the sensor installation unit protrusion 3113. Since the sensor installation unit 3110 and the display unit 3120 are disposed at the side portion 3100 to be adjacent to one another, the adhesive-type insect trap allows efficient utilization of the internal space of the main body 410. In addition, with the display unit 3120 including the indication light source guide 3122 and the display unit protrusion 3123, the adhesive-type insect trap can improve illuminance detection efficiency and accuracy of the illuminance sensor.

As described in the above embodiments, an adhesive-type insect trap includes: a main body having an adhesive sheet insertion hole; a light source mount disposed on the main body; and a cover detachably attached to the main body and having a through-hole formed in at least a portion thereof. The main body further includes a light source seat disposed to face the light source mount such that one side of a light source is mounted on the light source mount and the other side of the light source is mounted on the light source seat.

As described in the above embodiments, an adhesive-type insect trap includes: a main body having an adhesive sheet insertion hole; a light source mount disposed on the main body; and a cover detachably attached to the main body and having a through-hole formed in at least a portion thereof; and the adhesive-type insect trap further includes a sensor.

The adhesive-type insect trap according to embodiments of the present disclosure can prevent the interior of the insect trap, particularly, insects collected therein, from being visibly observed from the outside while securing high insect trapping efficiency. In addition, the adhesive-type insect trap according to the embodiments of the present disclosure may include an adhesive sheet secured to a main body thereof, thereby preventing the adhesive sheet having insects collected thereon from being easily separated from the main body. Further, the adhesive-type insect trap according to the embodiments of the present disclosure allows light emitted from a light source thereof to be refracted or spread, thereby improving insect attraction efficiency with decoy light.

Further, the adhesive-type insect trap according to the embodiments of the present disclosure may emit UV light to attract insects and may generate carbon dioxide, thereby further improving an insect attraction effect. Further, the adhesive-type insect trap according to the embodiments of the present disclosure has a deodorization effect, thereby providing a pleasant environment around the adhesive-type insect trap. Further, the adhesive-type insect trap according to the embodiments of the present disclosure may be provided with a light source for sterilization, thereby enabling killing of insects or sterilization of bacteria in insects trapped on the adhesive sheet within the insect trap.

Further, the adhesive-type insect trap according to the embodiments of the present disclosure may be provided with a camera or a sensor to allow a user to monitor the kind of insect trapped on the adhesive sheet or to determine a time for replacement of the adhesive sheet, may have an alarm function to inform a user of the time for replacement of the adhesive sheet, thereby improving user convenience, and may automatically or manually control the intensity of light emitted from a light source depending upon the quantity of light around the adhesive-type insect trap, thereby enabling economically feasible power consumption and extension of lifespan of the light source while improving insect attraction efficiency with decoy light. Further, the adhesive-type insect trap according to the embodiments of the present disclosure may include an insect attractant spray or an adhesive sheet containing an insect attractant, thereby improving insect attraction efficiency.

Although some embodiments have been described herein, it should be understood that these embodiments are provided for illustration only and are not to be construed in any way as limiting the present disclosure, and that the scope of the present disclosure should be defined by the appended claims and equivalents thereof.

The invention claimed is:

1. An adhesive-type insect trap comprising:
   a main body having an adhesive sheet insertion hole;
   a light source mount disposed on the main body;
   a cover detachably attached to the main body and having a through-hole formed in at least a portion thereof,
   an adhesive sheet guided into the main body via the adhesive sheet insertion hole;
   a light source mounted on the light source mount; and
   a sensor operable to detect:
      at least one kind of insect trapped on the adhesive sheet,
      an area of the adhesive sheet trapping insects, brightness of the adhesive sheet,
      an ambient temperature of a light source,
      intensity of light emitted from the light source,
      ambient illuminance of the insect trap,
      a time for replacement of the adhesive sheet,
      insertion of the adhesive sheet into the insect trap, and
      attachment of the cover to the insect trap;
   wherein the sensor further comprises an illuminance sensor for detecting illuminance of ambient light around the adhesive-type insect trap;
   wherein:
      a drive voltage applied to the light source mounted on the light source mount is controlled through PWM (Pulse Width Modulation) depending upon variation in illuminance of ambient light; and
      the drive voltage applied to the light source has at least two duty ratios;
      a first duty ratio of the drive voltage applied to the light source is s % when the illuminance of ambient light detected by the illuminance sensor is less than a preset illuminance range;
      a second duty ratio of the drive voltage applied to the light source is b % when the illuminance of ambient light detected by the illuminance sensor exceeds the preset illuminance range; and
      the first and the second duty ratios of the drive voltage satisfy a relationship: b>s.

2. The adhesive-type insect trap according to claim 1, wherein the main body further comprises a side portion connected to at least a portion of the light source mount and the side portion is further provided with a display unit.

3. The adhesive-type insect trap according to claim 1, wherein the sensor further comprises a UV sensor measuring the intensity of light emitted from the light source; and
   wherein the light source mounted on the light source mount further comprises a light emitting diode and the UV sensor measures intensity of light emitted from the light emitting diode.

4. The adhesive-type insect trap according to claim 3, wherein, when the intensity of light emitted from the light emitting diode and measured by the UV sensor is less than a preset value, the adhesive-type insect trap generates a light source replacement signal.

5. The adhesive-type insect trap according to claim 1, wherein the light source comprises a plurality of light emitting diodes, the plurality of light emitting diodes being controlled to be sequentially turned on/off.

6. The adhesive-type insect trap according to claim 1, wherein the illuminance sensor comprises at least three preset illuminance ranges and the drive voltage applied to the light source is controlled to have a duty ratio changed depending upon variation in illuminance range.

7. The adhesive-type insect trap according to claim 1, wherein the light source further comprises a support member and a light emitting diode disposed on the support member, and the sensor further comprises a UV sensor provided to the support member to measure the intensity of light emitted from the light source.

* * * * *